(12) United States Patent
Funahashi

(10) Patent No.: US 7,834,214 B2
(45) Date of Patent: *Nov. 16, 2010

(54) AROMATIC AMINE DERIVATIVE AND ORGANIC ELECTROLUMINESCENCE DEVICE EMPLOYING THE SAME

(75) Inventor: Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 25 days.

This patent is subject to a terminal disclaimer.

(21) Appl. No.: 12/259,514

(22) Filed: Oct. 28, 2008

(65) Prior Publication Data

US 2009/0058284 A1 Mar. 5, 2009

Related U.S. Application Data

(63) Continuation of application No. 11/316,942, filed on Dec. 27, 2005, now Pat. No. 7,470,472, which is a continuation of application No. PCT/JP2005/011105, filed on Jun. 17, 2005.

(30) Foreign Application Priority Data

Jun. 28, 2004 (JP) ............................. 2004-189368

(51) Int. Cl.
*H01L 51/54* (2006.01)
*H05B 33/14* (2006.01)
*C09K 11/06* (2006.01)
*C07C 211/58* (2006.01)
*C07F 7/02* (2006.01)

(52) U.S. Cl. ...................... 564/429; 564/305; 564/308; 428/690; 428/917; 257/40; 313/504; 313/506

(58) Field of Classification Search ...................... None
See application file for complete search history.

(56) References Cited

U.S. PATENT DOCUMENTS

| | | | |
|---|---|---|---|
| 5,667,925 A | 9/1997 | Tsuruoka et al. | 430/58.75 |
| 6,468,675 B1 | 10/2002 | Ishikawa et al. | 428/690 |
| 7,471,472 B2 * | 12/2008 | Ayame et al. | 359/819 |
| 2005/0064233 A1 | 3/2005 | Matsuura et al. | 428/690 |
| 2005/0214567 A1 * | 9/2005 | Parton et al. | 428/690 |
| 2005/0234256 A1 | 10/2005 | Marks et al. | 556/413 |

FOREIGN PATENT DOCUMENTS

| | | |
|---|---|---|
| EP | 0 879 686 | 11/1998 |
| JP | 8-305053 | 11/1996 |
| JP | 11-176574 | 7/1999 |
| JP | 11-219787 | 8/1999 |
| JP | 11-273860 | 10/1999 |
| JP | 2001-039934 | 2/2001 |

\* cited by examiner

*Primary Examiner*—D. Lawrence Tarazano
*Assistant Examiner*—Camie S Thompson
(74) *Attorney, Agent, or Firm*—Oblon, Spivak, McClelland, Maier & Neustadt, L.L.P.

(57) ABSTRACT

A specified aromatic amine derivative having a naphthalene structure bonding to diphenylamino group with a substituent. An organic electroluminescence device which comprises at least one organic thin film layer comprising a light emitting layer sandwiched between a pair of electrode consisting of an anode and a cathode, wherein at least one of the organic thin film layer comprises the aromatic amine derivative singly or as its mixture component. Organic electroluminescence devices having a long lifetime and a high efficiency of light emission, and aromatic amine derivatives capable of realizing such organic EL devices are provided.

13 Claims, 5 Drawing Sheets

AROMATIC AMINE DERIVATIVE AND ORGANIC ELECTROLUMINESCENCE DEVICE EMPLOYING THE SAME

REFERENCE TO PRIOR APPLICATIONS

This application is a Continuation application of U.S. application Ser. No. 11/316,942, filed Dec. 27, 2005, now pending, incorporated herein by reference, which is a Continuation of PCT/JP05/11105, filed Jun. 17, 2005; which claims the benefit of Japan 2004-189368, filed Jun. 28, 2004.

TECHNICAL FIELD

The present invention relates to an aromatic amine derivative and an organic electroluminescence ("electroluminescence" will be referred to as "EL", hereinafter) device employing the same and, more particularly, to an organic electroluminescence device having long lifetime, an enhanced efficiency of light emission and emitting blue light of a high purity and an aromatic amine derivative realizing the EL device.

BACKGROUND ART

Organic EL devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices operable at low driving voltage, with excellent luminance and favorable efficiency of light emission.

For example, there is disclosed such a technique using a single monoanthracene compound as an organic light-emitting material (refer to Patent Literature 1 below). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (refer to Patent Literature 2 below). However, in this technique, an efficiency of light emission obtained by using the material is also as low as about 1 to 3 cd/A. Therefore, further improvement of the technique has been demanded for rendering it practically usable. Further, there is disclosed a technique using a mono- or bis-anthracene compound together with a distearyl compound in an organic light emitting medium layer (refer to Patent Literature 3 below). However, the device described therein fails to show a sufficiently long half lifetime and, therefore, further improvement has been demanded.

Furthermore, a technique of employing mono- or bis-anthracene compound and a distyryl compound as an organic light emitting medium layer is disclosed (refer to Patent Literature 4 below). However, in these technology, a conjugated structure of the styryl compound lengthened wave length of a light emission spectrum and deteriorated the purity of color. Still further, Patent Literature 5 below, discloses a blue luminescence device with the use of diamino chrysene derivatives. However, despite the superiority in a light emission efficiency, because the device are not sufficient in its lifetime, further improvement was required.

Patent Literature 1: Japanese Unexamined Patent Application Laid-Open No. Hei 11-3782A
Patent Literature 2: Japanese Unexamined Patent Application Laid-Open No. Hei 8-012600
Patent Literature 3: International Application Published under PCT No. WO 00/06157
Patent Literature 4: Japanese Unexamined Patent Application Laid-Open No. 2001-284050
Patent Literature 5: Japanese Unexamined Patent Application Laid-Open No. Hei 11-273860

DISCLOSURE OF THE INVENTION

The present invention has been made to overcome the above problems and has an object of providing an organic EL device which emits blue light with high purity and of long lifetime, and an object of providing an anthracene derivative realizing the EL device.

As a result of extensive researches for developing aromatic amine derivatives having the above suitable properties and organic EL devices using the aromatic amine derivatives, the inventors have found that the object of the present invention can be achieved by employing an aromatic amine derivative represented by any one of following general formulae (1) to (4) whose naphthalene structure is bonded with a diphenylamino group having a substituent. Such being the case, the present invention has been accomplished on the basis of the foregoing findings and information.

Namely, the present invention provides an aromatic amine derivative represented by any one of following general formulae (1) to (4):

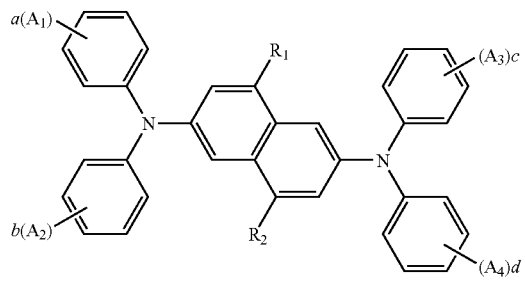

In the general formula (1), $R_1$ and $R_2$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a cyano group or a halogen atom;

In the general formula (1), $A_1$ to $A_4$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group or a halogen atom;

a, b, c and d each independently represents an integer of 0 to 5; when a, b, c and d each are 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring.

However, a case where both of $R_1$ and $R_2$ in the general formula (1) are hydrogen atoms is excluded and further; a case where all of $A_1$ to $A_4$ in the general formula (1) are hydrogen atoms is also excluded.

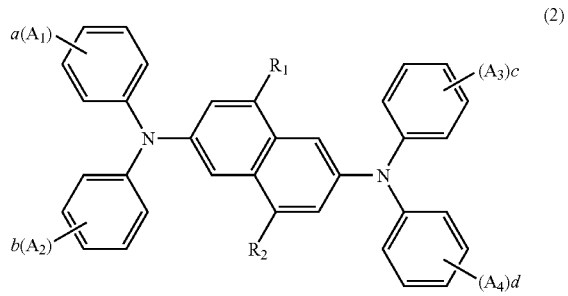

(2)

In the general formula (2), $R_1$, $R_2$, $A_1$ to $A_4$, a, b, c and d each independently represents the same as the foregoing description about themselves, and when each of a, b, c and d is 2 or greater, $A_1$ to $A_4$ may be the same with or different from each other and further, they may bond each other to form a saturated or unsaturated ring; a couple of $A_1$ and $A_2$, and a couple of $A_3$ and $A_4$ may bond each other to form a saturated or unsaturated ring.

However, a case where both of $R_1$ and $R_2$ in the general formula (2) are hydrogen atoms is excluded and further, at least one of $A_1$ to $A_4$ in the general formula (2) is a substituted or unsubstituted secondary or tertiary alkyl group having 3 to 10 carbon atoms.

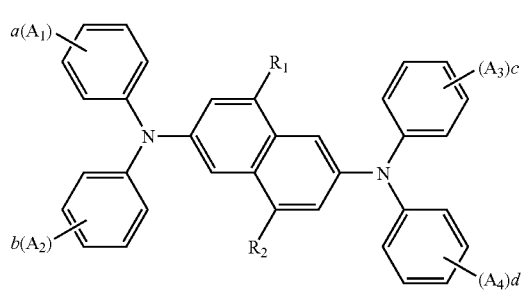

(3)

In the general formula (3), $R_1$, $R_2$, $A_1$ to $A_4$, a, b, c and d each independently represents the same as the foregoing description about themselves, and when each of a, b, c and d is 2 or greater, $A_1$ to $A_4$ may be the same with or different from each other and further, they may bond each other to form a saturated or unsaturated ring; a couple of $A_1$ and $A_2$, and a couple of $A_3$ and $A_4$ may bond each other to form a saturated or unsaturated ring;

However, a case where both of $R_1$ and $R_2$ in the general formula (3) are hydrogen atoms is excluded and further, at least one of a, b, c and d is an integer of 2 or greater.

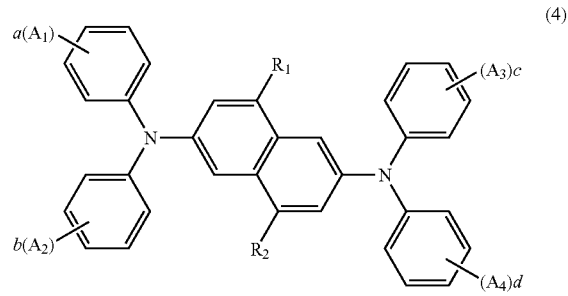

(4)

In the general formula (4), $R_1$, $R_2$, $A_1$ to $A_4$, a, b, c and d each independently represents the same as the foregoing description about themselves, and when each of a, b, c and d is 2 or greater, $A_1$ to $A_4$ may be the same with or different from each other and further, they may bond each other to form a saturated or unsaturated ring; a couple of $A_1$ and $A_2$, and a couple of $A_3$ and $A_4$ may bond each other to form a saturated or unsaturated ring.

However, $R_1$ and/or $R_2$ in the general formula (4) is a substituted or unsubstituted secondary or tertiary alkyl group having 3 to 10 carbon atoms and further, a case where all of $A_1$ to $A_4$ are hydrogen atoms is excluded.

Further, the present invention provides an organic EL device which comprises at least one organic thin film layer comprising a light emitting layer sandwiched between a pair of electrodes consisting of an anode and a cathode, wherein at least one of the organic thin film layers comprises the aromatic amine derivative singly or as its mixture component.

Also, the present invention provides an organic electroluminescence device which comprises at least one organic thin film layer comprising a light emitting layer sandwiched between a pair of electrodes consisting of an anode and a cathode, wherein at least one of the organic thin film layer comprises the above aromatic amine derivative as an essential component between the anode and the light emitting layer.

The organic EL device employing the aromatic amine derivative of the present invention reveals practically sufficient luminance even under low applied voltage, exhibits an enhanced efficiency of light emission, and is resistant to degrade even after a long time usage demonstrating a prolonged lifetime.

PREFERRED EMBODIMENT TO CARRY OUT THE INVENTION

Figure 1:
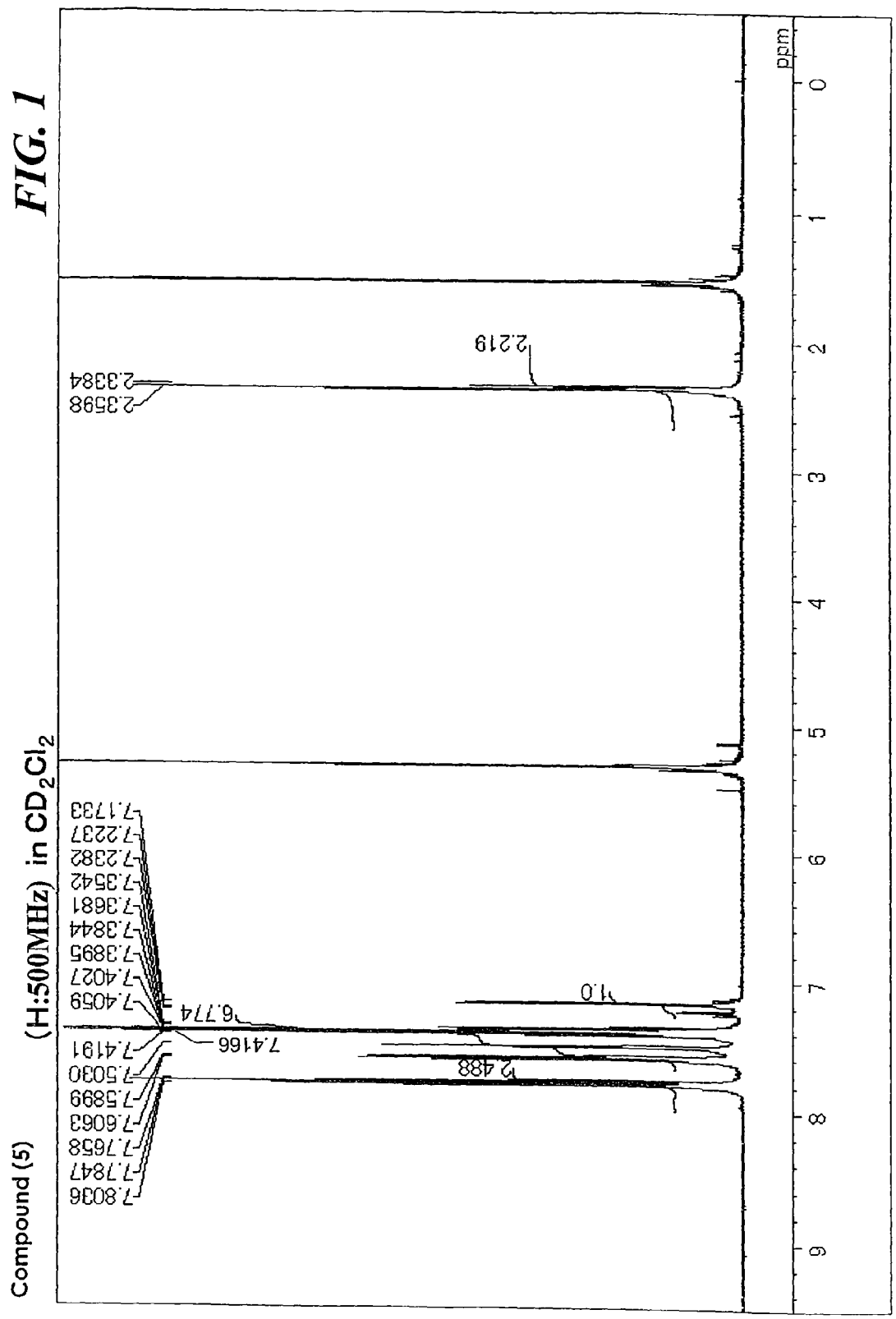
FIG. 1 is a chart showing a NMR spectrum about Compound (5) as the aromatic amine derivative of the present invention.

The present invention provides an aromatic amine derivative represented by any one of following general formulae (1) to (4):

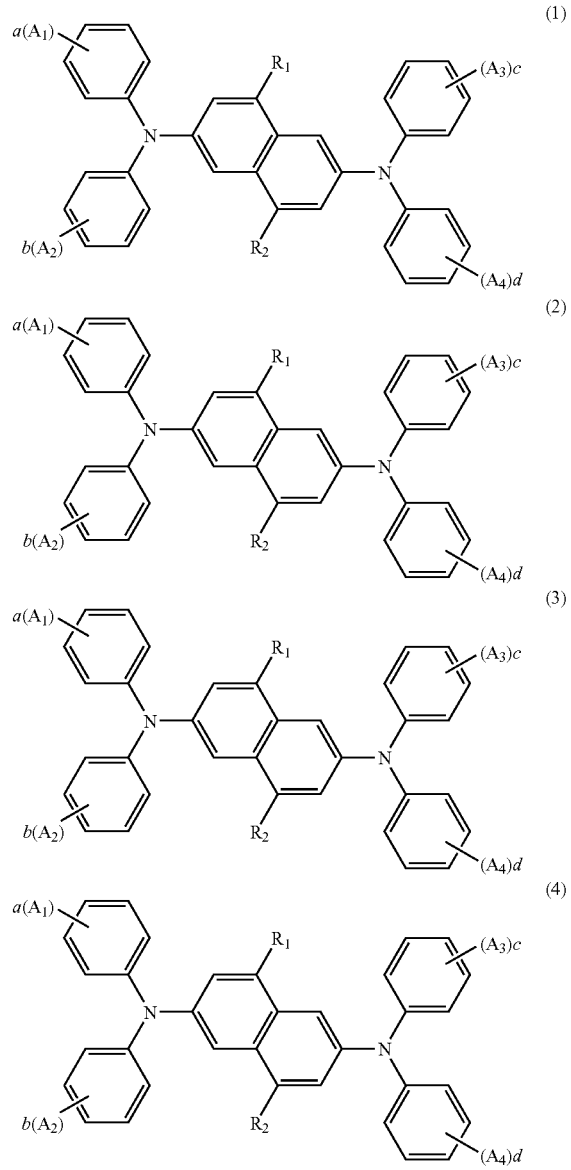

In the general formulae (1) to (4), $R_1$ and $R_2$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) carbon atoms, a substituted or unsubstituted aralkyl group having 1 to 50 (preferably 9 to 20) carbon atoms, a substituted or unsubstituted cycloalkyl group having 3 to 50 (preferably 5 to 12) carbon atoms, a substituted or unsubstituted alkoxyl group having 1 to 50 (preferably 1 to 6) carbon atoms, a substituted or unsubstituted aryloxy group having 5 to 50 (preferably 5 to 18) carbon atoms, a substituted or unsubstituted arylamino group having 5 to 50 (preferably 5 to 18) carbon atoms, a substituted or unsubstituted alkylamino group having 1 to 20 (preferably 1 to 6) carbon atoms, or a halogen atom.

Examples of the substituted or unsubstituted alkyl group represented by $R_1$ or $R_2$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenyl benzyl group, α,α-di trifluoromethyl benzyl group, triphenylmethyl group, α-benzyloxybenzyl group, etc.

Examples of the substituted or unsubstituted aryl group represented by $R_1$ or $R_2$ include phenyl group, 2-methylphenyl group, 3-methylphenyl group, 4-methylphenyl group, 4-ethylphenyl group, biphenyl group, 4-methyl biphenyl group, 4-ethylbiphenyl group, 4-cyclohexylbiphenyl group, terphenyl group, 3,5-dichlorophenyl group, naphthyl group, 5-methylnaphthyl group, anthryl group, pyrenyl group, etc.

Examples of the substituted or unsubstituted aralkyl group represented by $R_1$ or $R_2$ include benzyl group, α,α-methylphenylbenzyl group, triphenylmethyl group, 1-phenylethyl group, 2-phenylethyl group, 1-phenylisopropyl group, 2-phenylisopropyl group, phenyl-t-butyl group, -naphthylmethyl group, 1-α-naphthylethyl group, 2-α-naphthylethy group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, α-phenoxybenzyl group, α-benzyloxy benzyl group, α,α-ditrifluoromethylbenzyl group, 1-pyrrolylmethyl group, 2-(1-pyrrolyl)ethyl, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the cycloalkyl group represented by $R_1$ or $R_2$ include cyclopropyl group, cyclobutyl group, cyclopentyl group, cyclohexyl group, norbornene group, adamanthyl group, etc.

Examples of the alkoxyl group represented by $R_1$ or $R_2$ include methoxy group, ethoxy group, propoxy group, isopropoxy group, butoxy group, isobutoxy group, s-butoxy group, t-butoxy group, various pentyloxy groups, various hexyloxy groups, etc.

Examples of the aryloxy group represented by $R_1$ or $R_2$ include phenoxy group, tolyloxy group, naphthyloxy group, etc.

Examples of the arylamino group represented by $R_1$ or $R_2$ include diphenylamino group, ditolylamino group, isopropyldiphenylamino group, t-butyldiphenylamino group, diisopropyldiphenylamino group, di-t-butyldiphenylamino group, dinaphthylamino group, naphthylphenylamino group, etc.

Examples of the alkylamino group represented by $R_1$ or $R_2$ include dimethylamino group, diethylamino group, dihexylamino group, etc.

Examples of the halogen atom represented by $R_1$ or $R_2$ include fluorine atom, chlorine atom, bromine atom, etc.

Among those, methyl group, ethyl group, propyl group, isopropyl group, butyl group, sec-butyl group, tert-butyl group, cyclopentyl group, cyclohexyl group, phenyl group, naphthyl group and 4-methylphenyl group are preferable as $R_1$ or $R_2$, while methyl group, ethyl group, propyl group, isopropyl group, cyclohexyl group, phenyl group and naphthyl group being more preferable.

In the general formulae (1) to (4), $A_1$ to $A_4$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) carbon atoms, a substituted or unsubstituted aralkyl group having 1 to 50 (preferably 9 to 20) carbon atoms, a substituted or unsubstituted cycloalkyl group having 3 to 50 (preferably 5 to 12) carbon atoms, a substituted or unsubstituted alkoxyl group having 1 to 50 (preferably 1 to 6) carbon atoms, a substituted or unsubstituted aryloxy group having 5 to 50 (preferably 5 to 18) carbon atoms, a substituted or unsubstituted arylamino group having 5 to 50 (preferably 5 to 18) carbon atoms, a substituted or unsubstituted alkylamino group having 1 to 20 (preferably 1 to 6) carbon atoms, a substituted or unsubstituted silyl group or a halogen atom.

Among those, a hydrogen atom, a substituted or unsubstituted alkyl group having 1 to 10 carbon atoms, a substituted or unsubstituted aryl group having 5 to 20 carbon atoms, a substituted or unsubstituted aralkyl group having 1 to 20 carbon atoms, a substituted or unsubstituted cycloalkyl group having 3 to 10 carbon atoms or a substituted or unsubstituted silyl group is preferable as $A_1$ to $A_4$; while a hydrogen atom, a substituted or unsubstituted alkyl group having 1 to 4 carbon atoms, a substituted or unsubstituted aryl group having 5 to 18 carbon atoms, a substituted or unsubstituted aralkyl group having 1 to 18 carbon atoms, a substituted or unsubstituted cycloalkyl group having 3 to 6 carbon atoms or a substituted or unsubstituted silyl group is more preferable as $A_1$ to $A_4$.

Further, it is preferable that at least one of $A_1$ to $A_4$ is a substituted or unsubstituted silyl group.

Specific examples of the alkyl group, the aryl group, the aralkyl group, the cycloalkyl group, the alkoxyl group, the aryloxy group, the arylamino group, the alkylamino group and the halogen atom as the above $A_1$ to $A_4$ are the same as described about the foregoing $R_1$ and $R_2$.

Examples of the substituted or unsubstituted silyl group represented by $A_1$ to $A_4$ include trimethylsilyl group, triethylsilyl group, t-butyldimethylsilyl group, vinyldimethylsilyl group, propyldimethylsilyl group, methyldiphenylsilyl group, dimethylphenylsilyl group, triphenylsilyl group, etc.

In the general formulae (1) to (4), a, b, c and d each independently represents an integer of 0 to 5, preferably an integer of 0 to 3, and more preferably an integer of 0 to 2.

When a, b, c and d each are 2 or more, plural of $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring;

However, a case where both of $R_1$ and $R_2$ in the general formula (1) are hydrogen atoms is excluded and further; a case where all of $A_1$ to $A_4$ in the general formula (1) are hydrogen atoms is also excluded.

Further, a case where both of $R_1$ and $R_2$ in the general formula (2) are hydrogen atoms is excluded and further, at least one of $A_1$ to $A_4$ in the general formula (2) is a substituted or unsubstituted secondary or tertiary alkyl group having 3 to 10 carbon atoms.

Furthermore, a case where both of $R_1$ and $R_2$ in the general formula (3) are hydrogen atoms is excluded and further, at least one of a, b, c and d is an integer of 2 or greater.

Still further, $R_1$ and/or $R_2$ in the general formula (4) is a substituted or unsubstituted secondary or tertiary alkyl group having 3 to 10 carbon atoms and further, a case where all of $A_1$ to $A_4$ are hydrogen atoms is excluded.

Specific examples of the aromatic amine derivatives represented by the general formulae (1) to (4) will be shown below, though not particularly limited thereto. Meanwhile, in the following compounds, Me represents a methyl group.

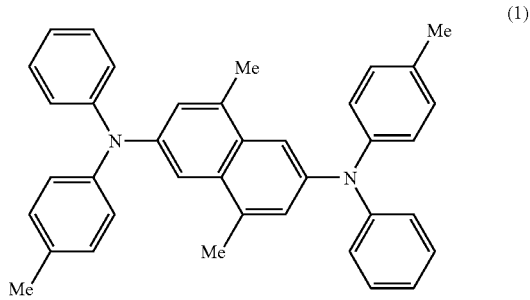

(1)

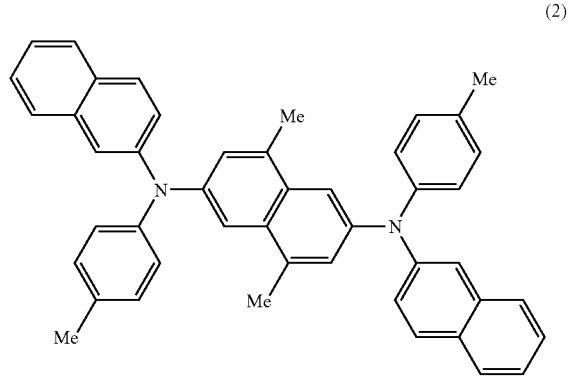

(2)

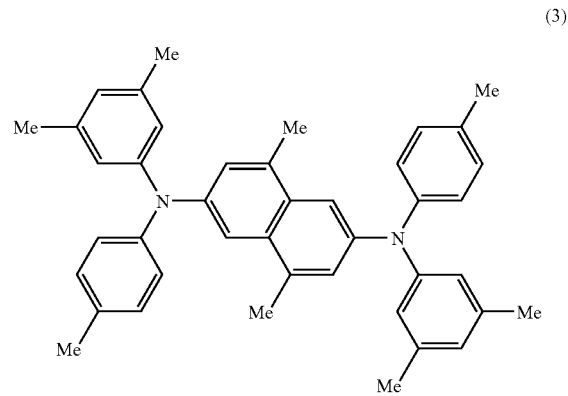

(3)

-continued
(4)
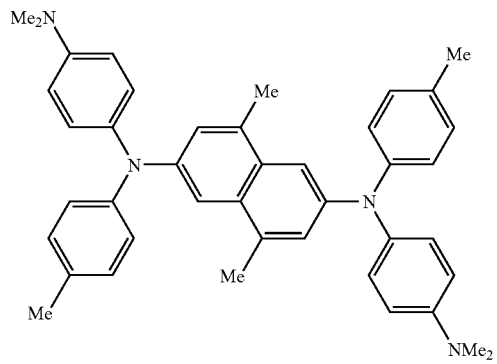
(5)
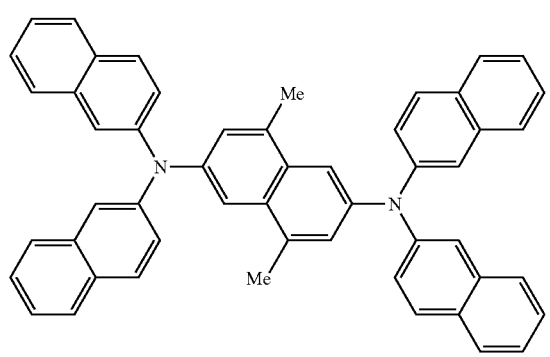
(6)
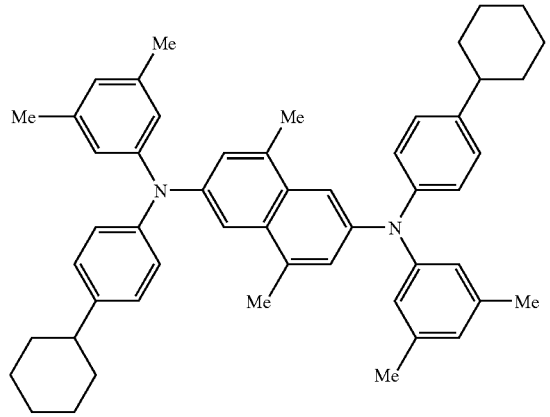
-continued
(7)
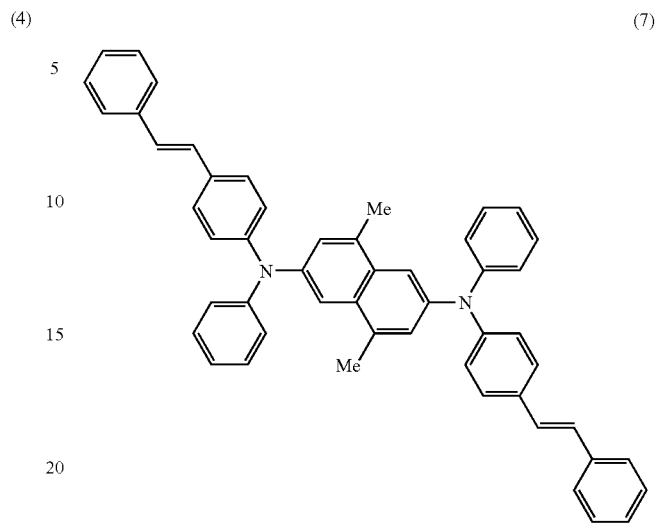
(8)
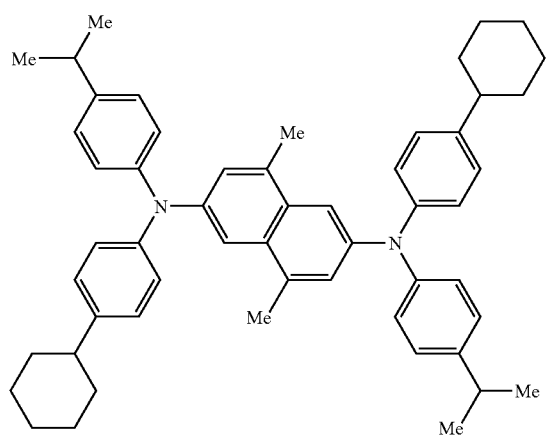
(9)
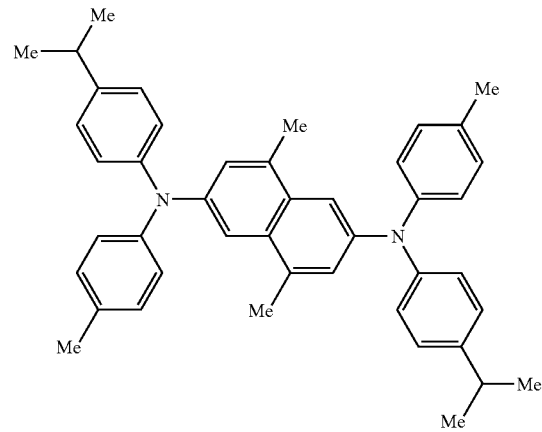

-continued
(10)
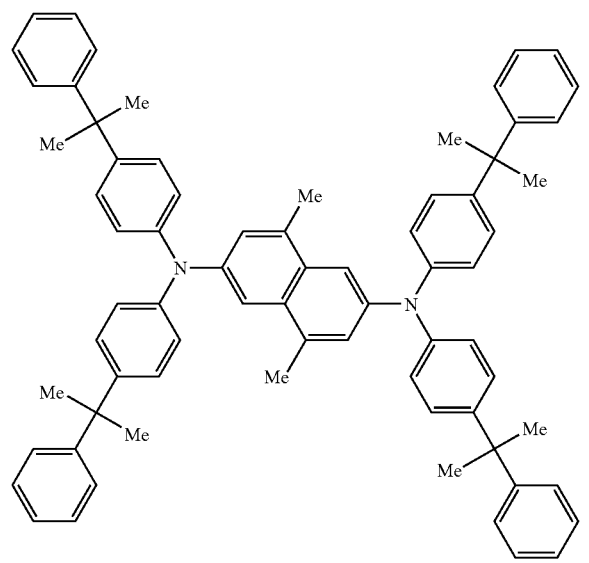
(11)
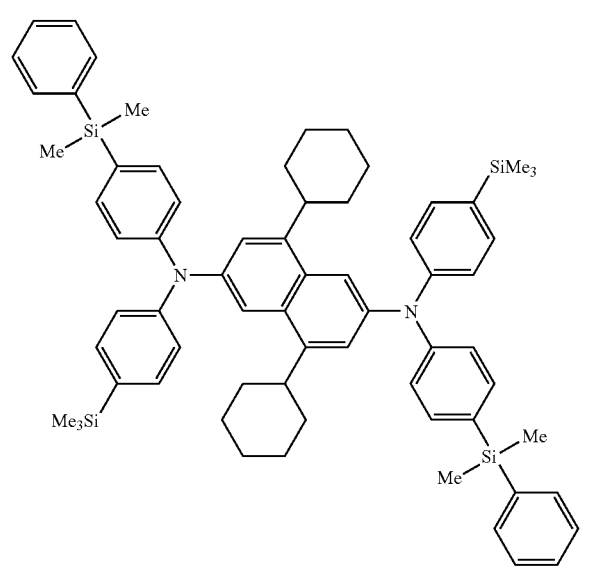
(12)
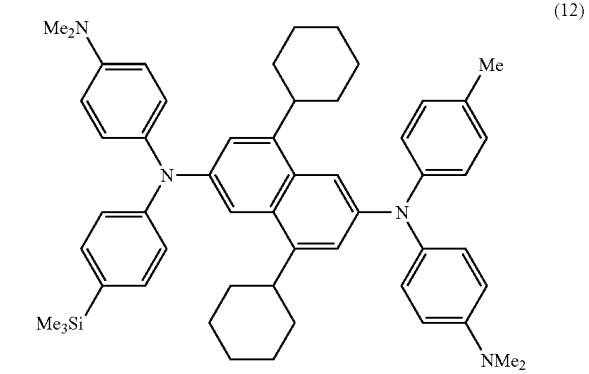
-continued
(13)
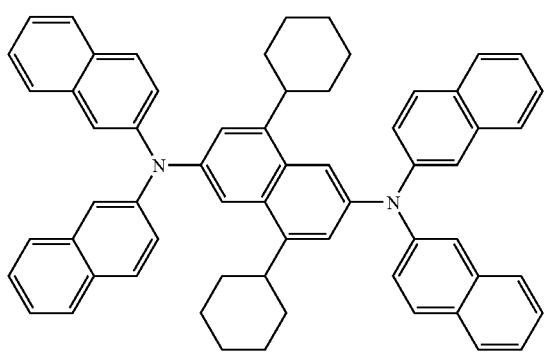
(14)
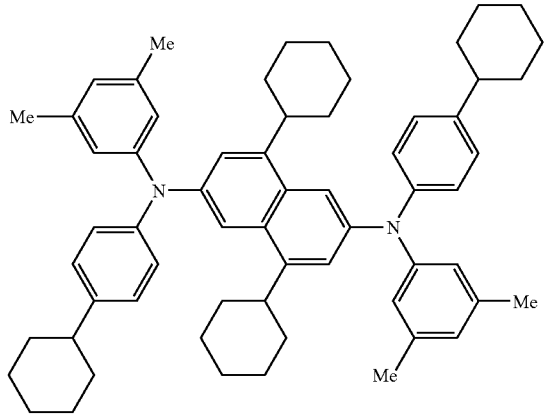
(15)
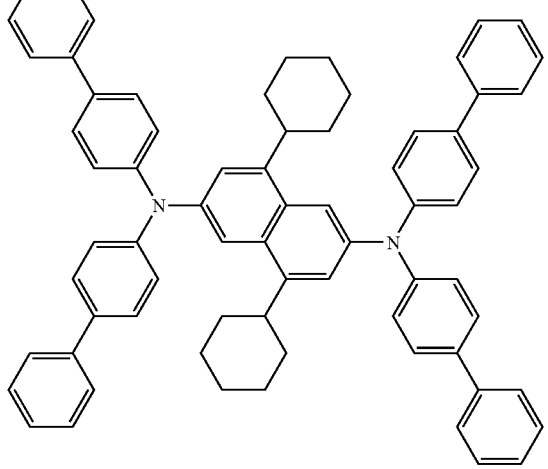

-continued
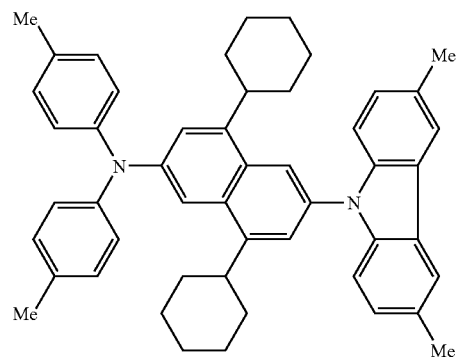
(16)
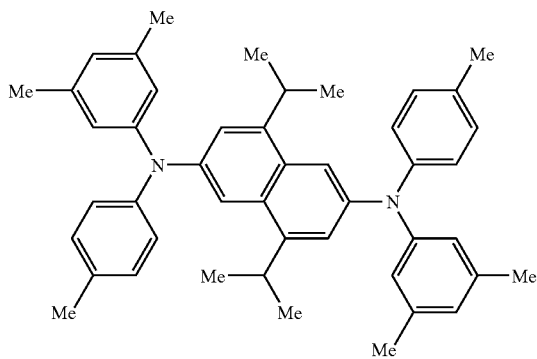
(20)
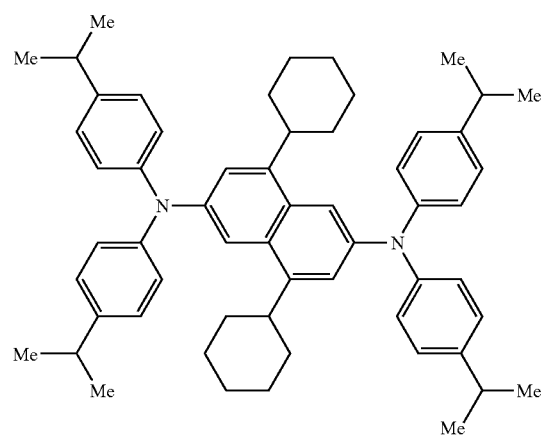
(17)
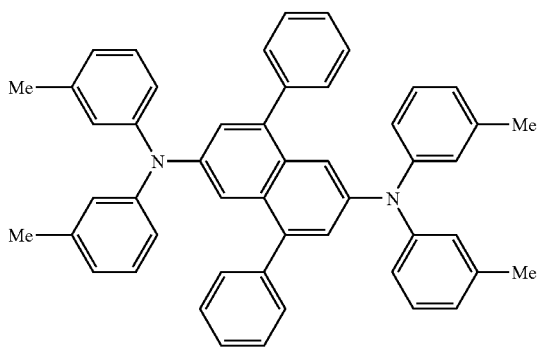
(21)
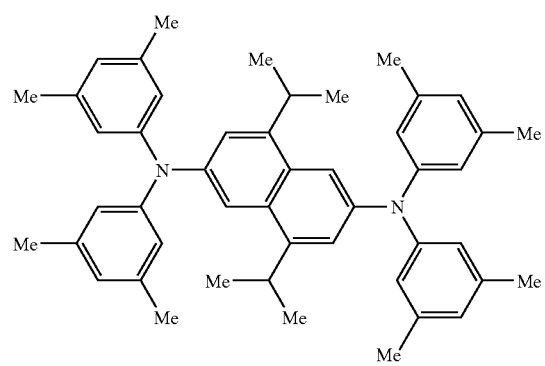
(18)
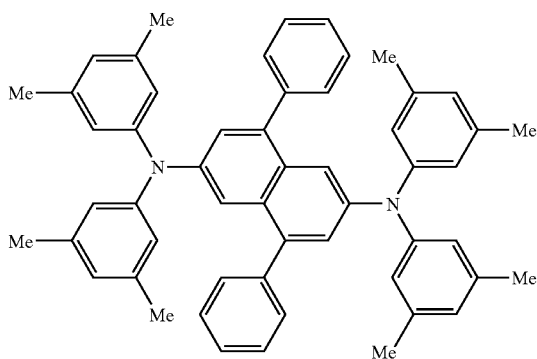
(22)
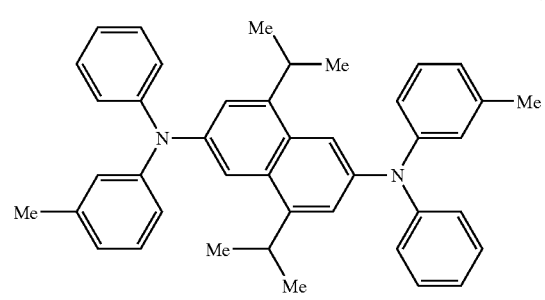
(19)
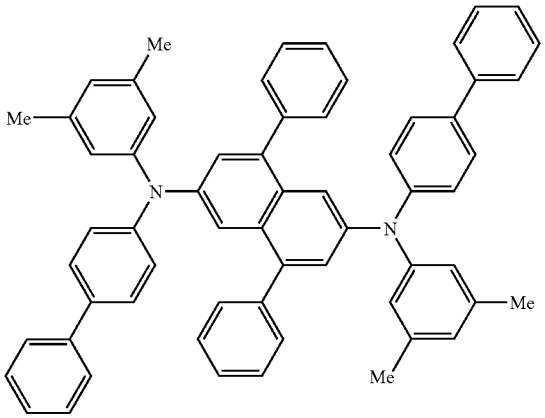
(23)

-continued
(24)
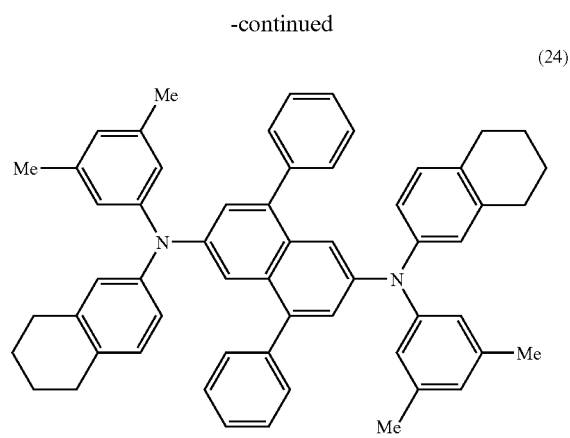
(27)
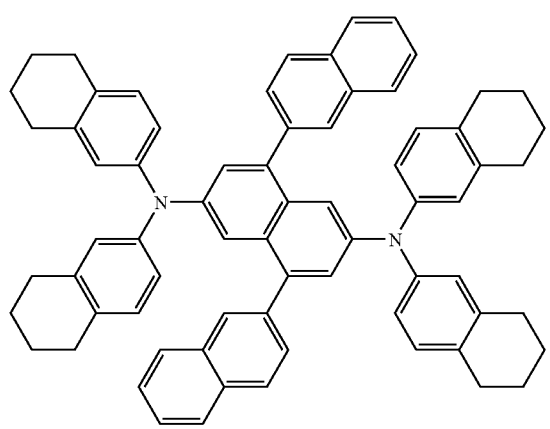
(25)
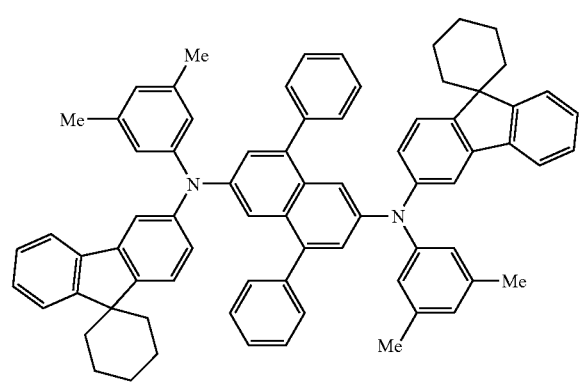
(28)
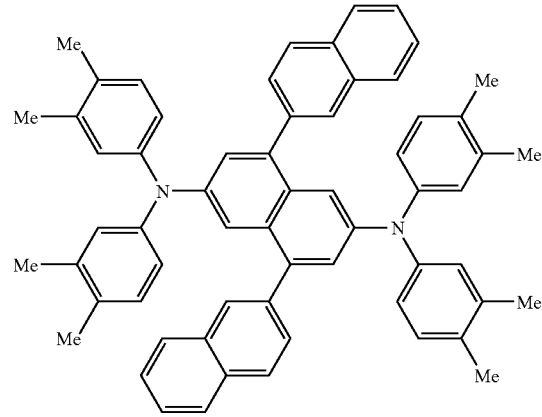
(26)
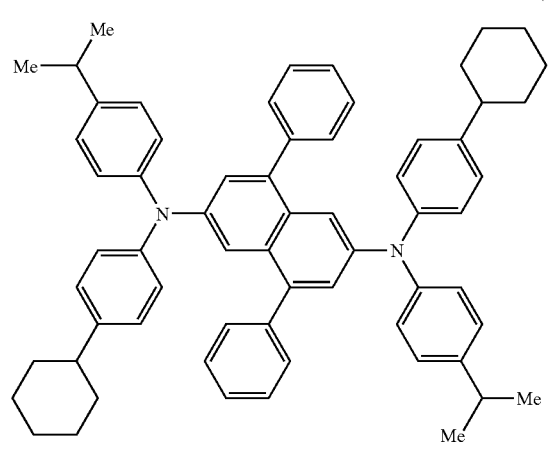
(29)
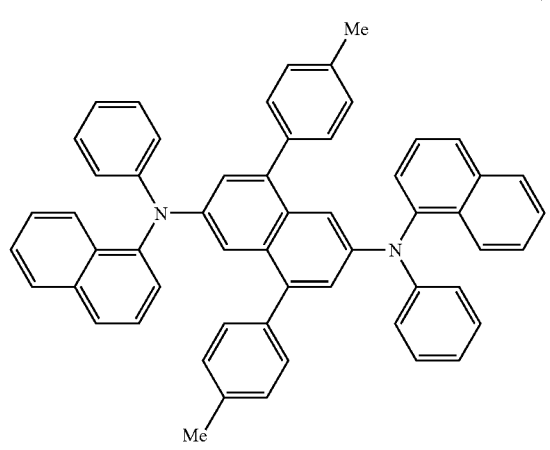

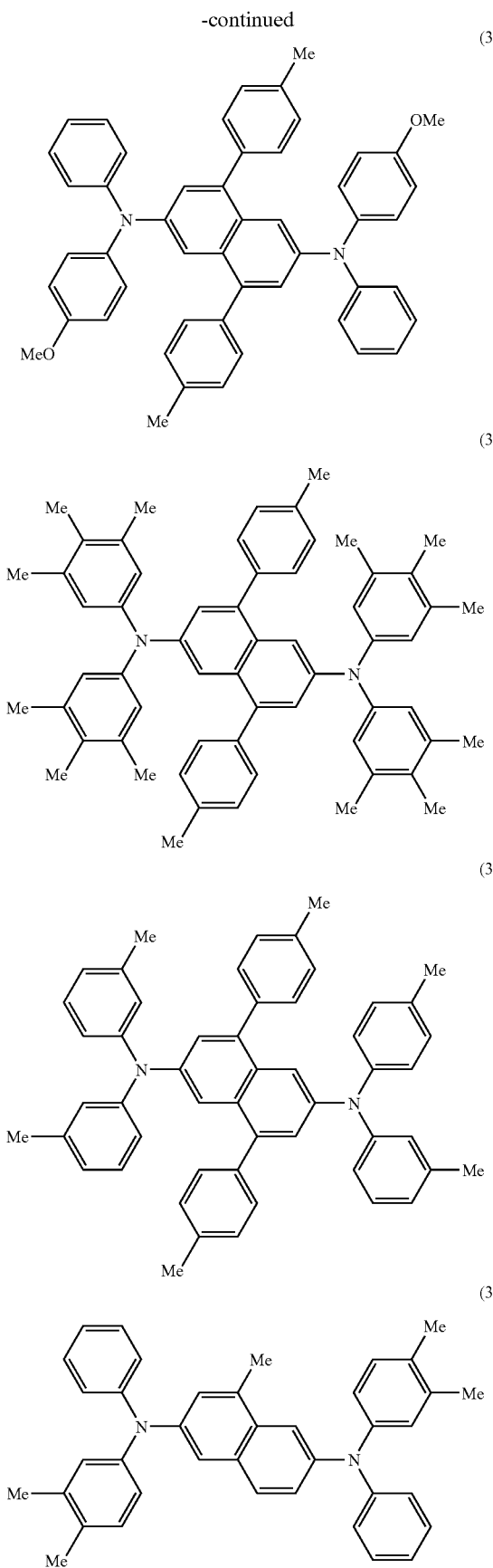

In the aromatic amine derivative represented by any of general formulae (1) to (4) of the present invention, since a benzene ring is connected to a diaminonaphthalene structure as a light emission center, the association between the compounds is prevented, resulting in a prolonged lifetime thereof. Further, an introduction of a bulky substituent for the naphthalene skeleton into a distant position (4-position, 8-position) from bonding location of the amino group (2-position, 6-position), the lifetime further prolongs because the association between the compounds is prevented without giving a steric repulsion against bonding between the amino group and naphthalene.

Further, the aromatic amine derivatives have a strong fluorescence in a solid state, and are excellent in field light emission, which leads to a fluorescent quantum efficiency as high as 0.3 or more. In addition, the aromatic amine derivatives of the present invention exhibit not only excellent capabilities of injecting and transporting holes from the metal electrode or organic thin film layers, but also excellent capabilities of injecting and transporting electrons from the metal electrode or organic thin film layers and, therefore, are usefully employable as light emitting materials for organic EL devices. Besides, the aromatic amine derivatives of the present invention may be used together with other hole transporting materials, electron transporting materials or doping materials.

The organic EL device of the present invention is a device comprising a film of organic compounds having a single layer or a plurality of layers sandwiched between an anode and a cathode. When the film of organic compounds has a single layer, a light emitting layer is sandwiched between the anode and the cathode. The light emitting layer contains the light emitting material and may further contain a hole injecting material and an electron injecting material in order to effectively transport holes injected from the anode or electrons injected from the cathode to the light emitting material. The aromatic amine derivatives represented by the general formulae (1) have a high light emitting property and excellent hole injecting ability and hole transporting ability as well as excellent electron injecting ability and electron transporting ability and, therefore, can be used as a light emitting material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention exhibit not only an extremely high fluorescent quantum efficiency but also high hole transporting ability and electron transporting ability, and further are capable of forming a uniform thin film, so that the light emitting layer may be formed from the aromatic amine derivatives only. On the other hand, in the case where the organic EL device of the present invention includes two or more organic thin film layers having at least the light emitting layer which are sandwiched between the cathode and anode, the organic thin film layers preferably include an organic layer containing the aromatic amine derivative of the present invention as an essential component which is sandwiched between the anode and the light emitting layer. Such an organic layer may be a hole injecting layer, a hole transporting layer, etc.

Further, in a case where the aromatic amine derivative of the present invention is employed as a doping material, it is preferable that at least one kind selected from the group consisting of anthracene derivatives of a following general formula (5), anthracene derivatives of a following general formula (6) and pyrene derivatives of a following general formula (7) is employed as a host material.

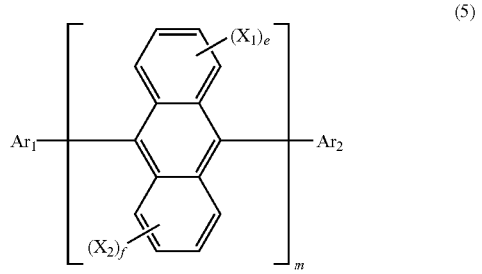

In the general formula (5), $X_1$ and $X_2$ each independently represents a hydrogen atom, a substituted or unsubstituted alkyl group having 1 to 50 carbon atoms, a substituted or unsubstituted aryl group having 5 to 50 nuclear carbon atoms, a substituted or unsubstituted aralkyl group having 6 to 50 nuclear carbon atoms, a substituted or unsubstituted cycloalkyl group having 3 to 50 nuclear carbon atoms, a substituted or unsubstituted alkoxyl group having 1 to 50 nuclear carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 20 carbon atoms, a substituted or unsubstituted heterocyclic group having 5 to 50 nuclear carbon atoms or a halogen atom; e and f each independently represents an integer of 0 to 4; when e and f are 2 or greater, $X_1$ and $X_2$ may be the same with or different from each other.

$Ar_1$ and $Ar_2$ each independently represents a substituted or unsubstituted aryl group having 5 to 50 nuclear carbon atoms or a substituted or unsubstituted heterocyclic group having 5 to 50 nuclear carbon atoms; at least one of $Ar_1$ or $Ar_2$ represents a substituted or unsubstituted aryl group with a condensed ring and having 10 to 50 nuclear carbon atoms; and m represents an integer of 1 to 3. When m is 2 or greater, a group within a parentheses: [ ] may be the same with or different from each other.

Specific examples and substituents of the $X_1$, $X_2$, $Ar_1$ and $Ar_2$ are the same as those explained about the foregoing general formulae (1) to (4).

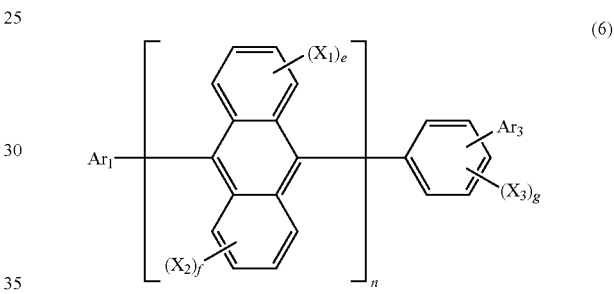

In the general formula (6), $X_1$ to $X_3$ each independently represents a hydrogen atom, a substituted or unsubstituted alkyl group having 1 to 50 carbon atoms, a substituted or unsubstituted aryl group having 5 to 50 nuclear carbon atoms, a substituted or unsubstituted aralkyl group having 6 to 50 nuclear carbon atoms, a substituted or unsubstituted cycloalkyl group having 3 to 50 nuclear carbon atoms, a substituted or unsubstituted alkoxyl group having 1 to 50 nuclear carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 20 carbon atoms, a substituted or unsubstituted heterocyclic group having 5 to 50 nuclear carbon atoms or a halogen atom; e, f, and g each independently represents an integer of 0 to 4. When e, f, and g are 2 or greater, $X_1$, $X_2$ and $X_3$ may be the same with or different from each other.

$Ar_1$ represents a substituted or unsubstituted aryl group with a condensed ring and having 10 to 50 nuclear carbon atoms and $Ar_3$ represents a substituted or unsubstituted aryl group having 5 to 50 nuclear carbon atoms; n represents an integer of 1 to 3. When n is 2 or greater, a group within a parentheses: [ ] may be the same with or different from each other.

Specific examples and substituents of the $X_1$ to $X_3$, $Ar_1$ and $Ar_3$ are the same as those explained about the foregoing general formulae (1) to (4).

Specific examples of anthracene derivative represented by the general formulae (5) and (6) will be shown below, though not particularly limited thereto.

AN1 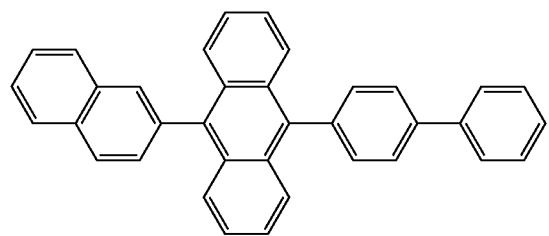
AN2 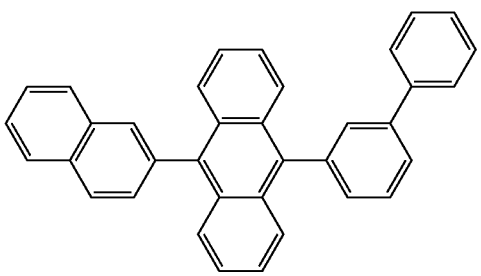
AN3 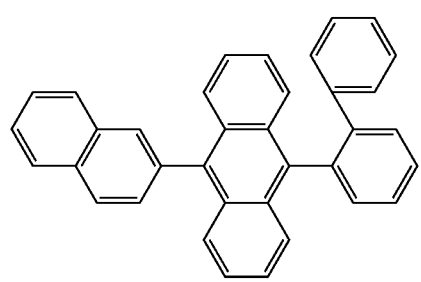
AN4 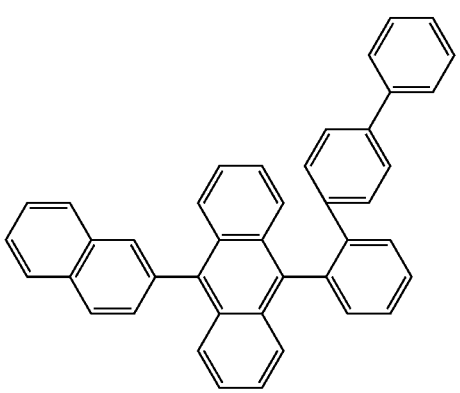
AN5 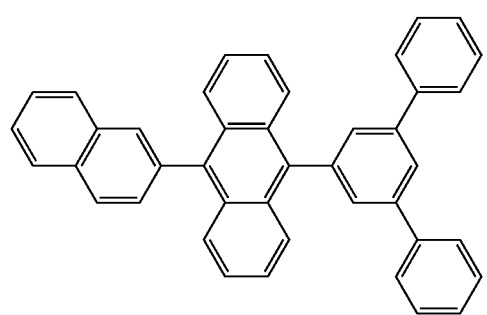
AN6 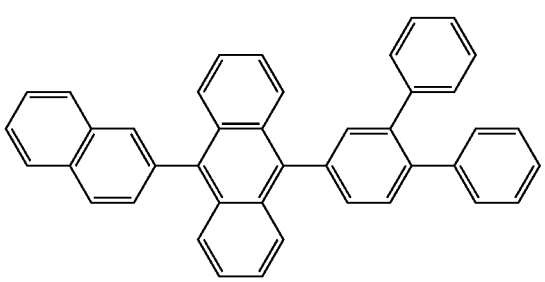
AN7 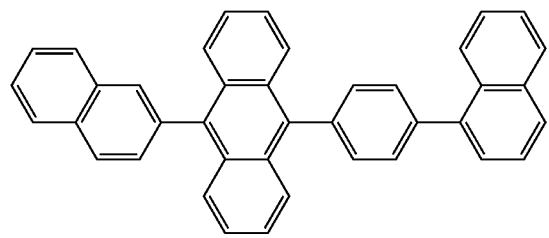
AN8 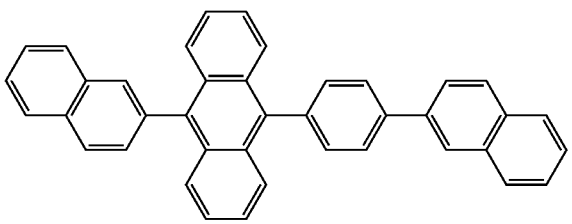
AN9 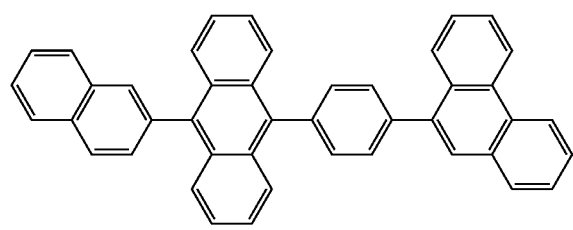
AN10 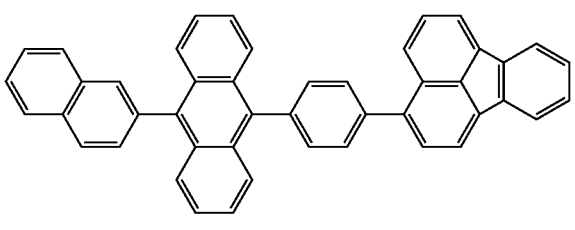

-continued
AN11
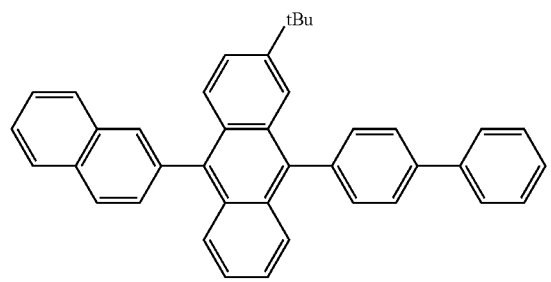
AN12
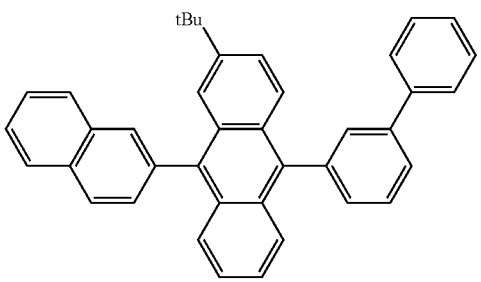
AN13
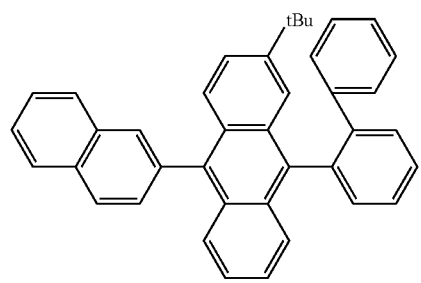
AN14
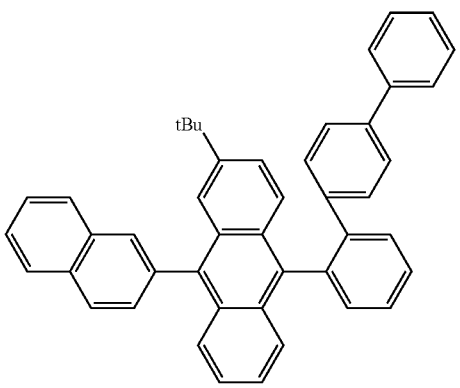
AN15
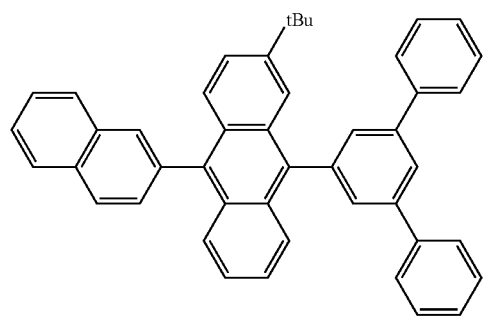
AN16
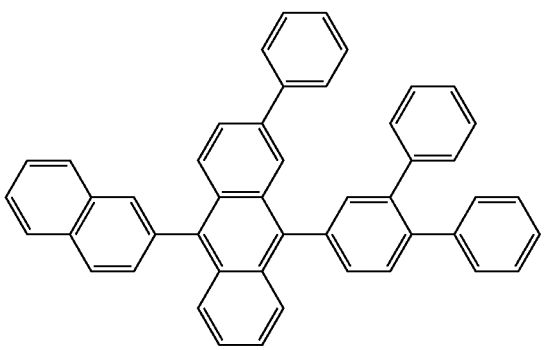
AN17
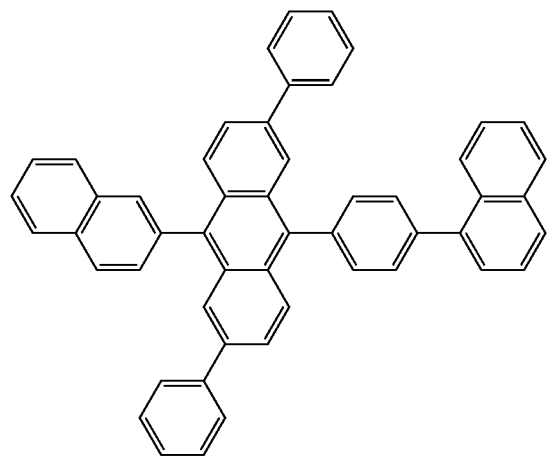
AN18
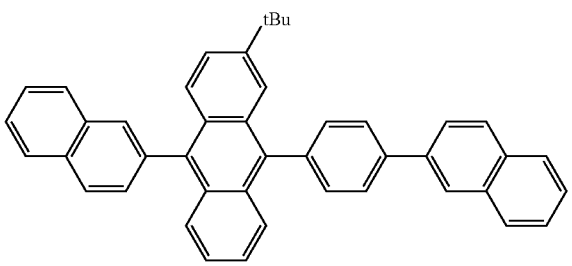

-continued
AN19
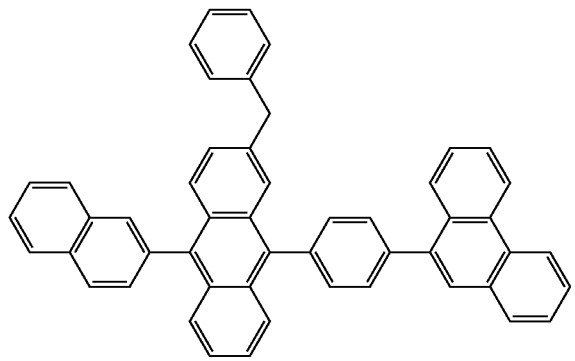
AN20
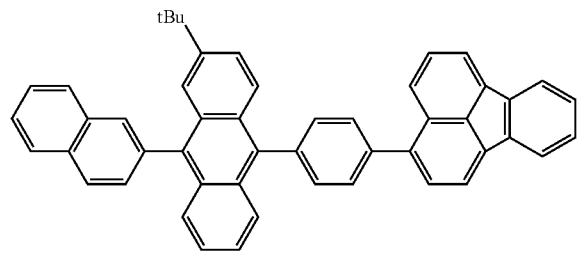
AN21
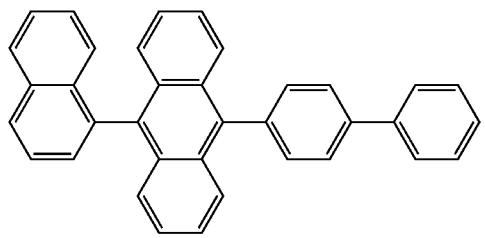
AN22
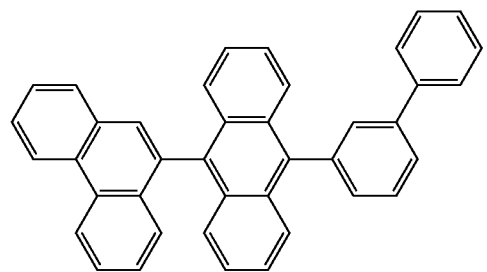
AN23
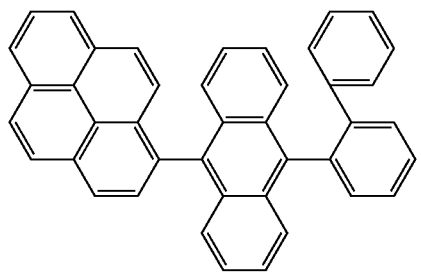
AN24
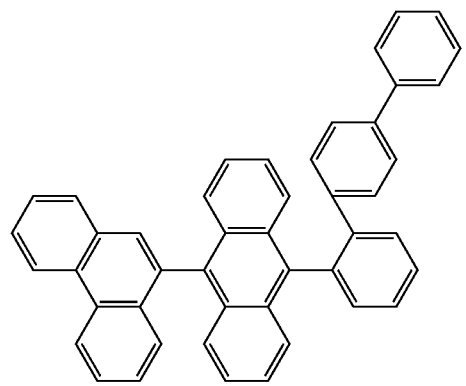
AN25
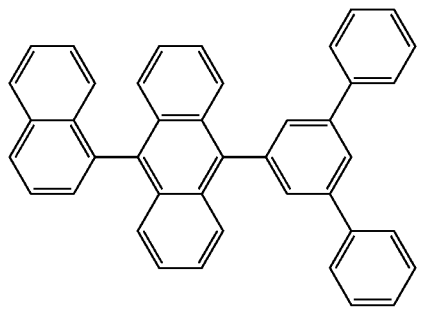
AN26
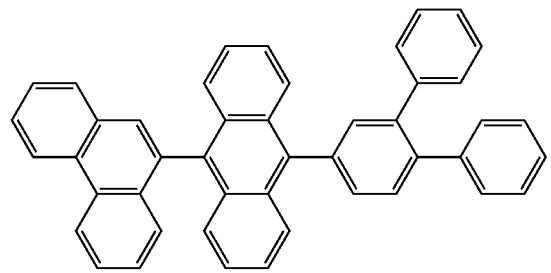
AN27
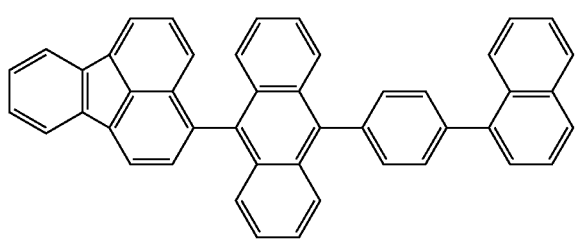
AN28
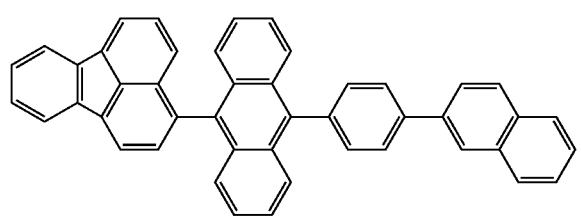

-continued
AN29
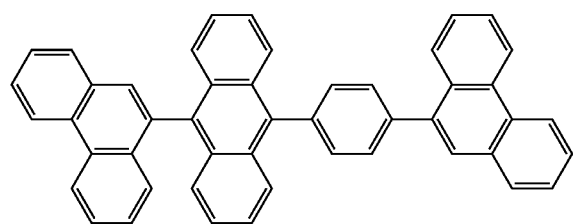
AN30
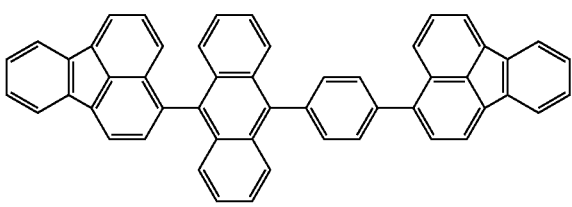
AN31
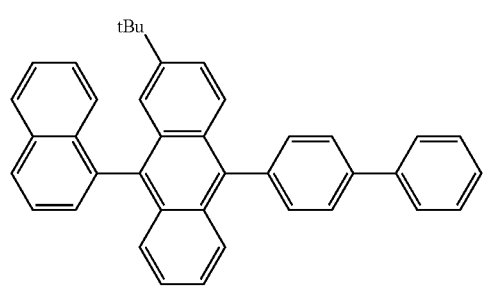
AN32
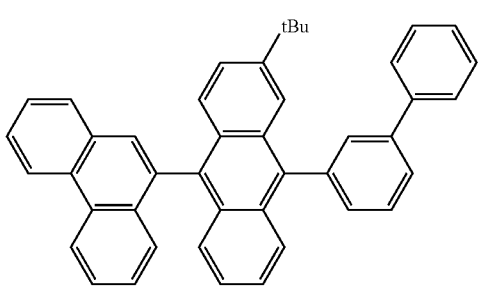
AN33
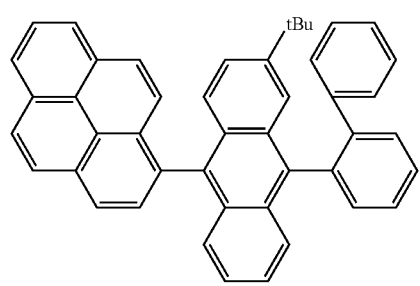
AN34
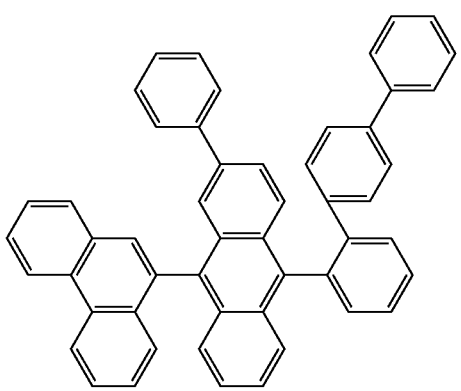
AN35
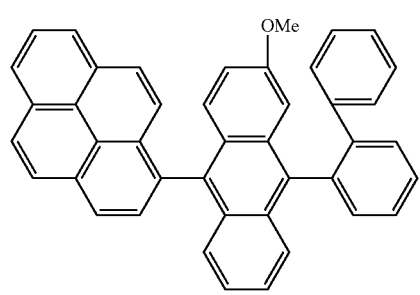
AN36
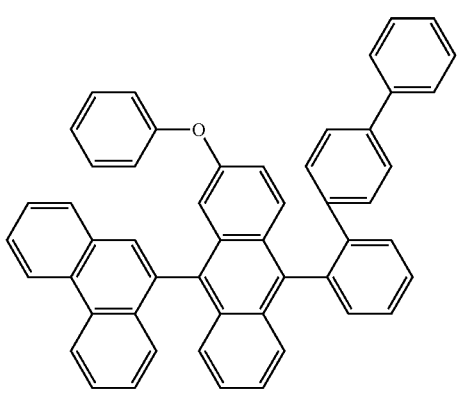
AN37
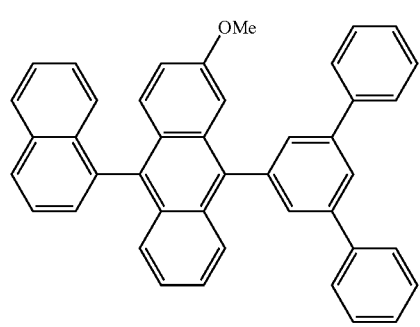
AN38
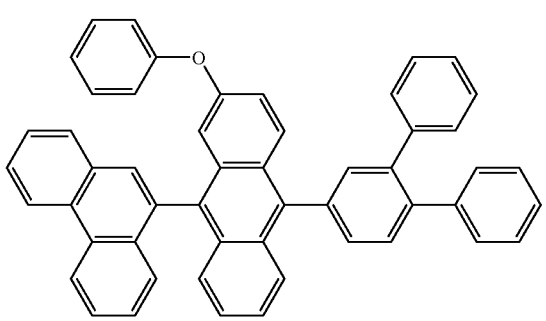

-continued
AN39
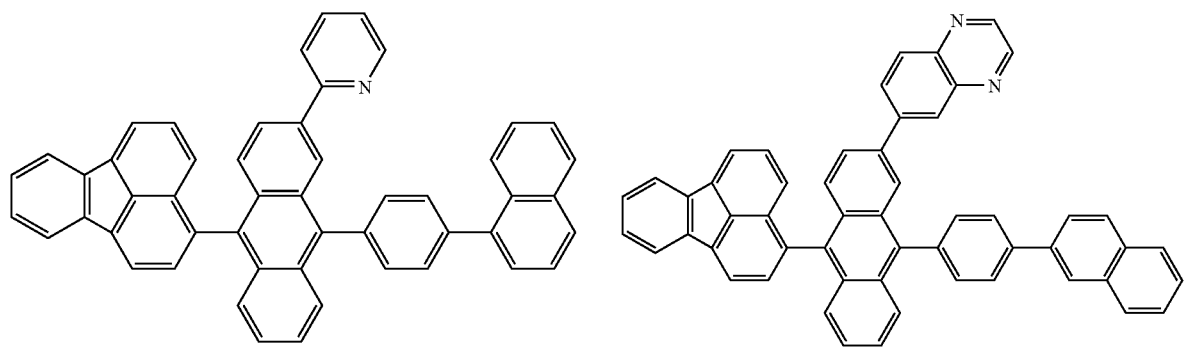
AN40
AN41
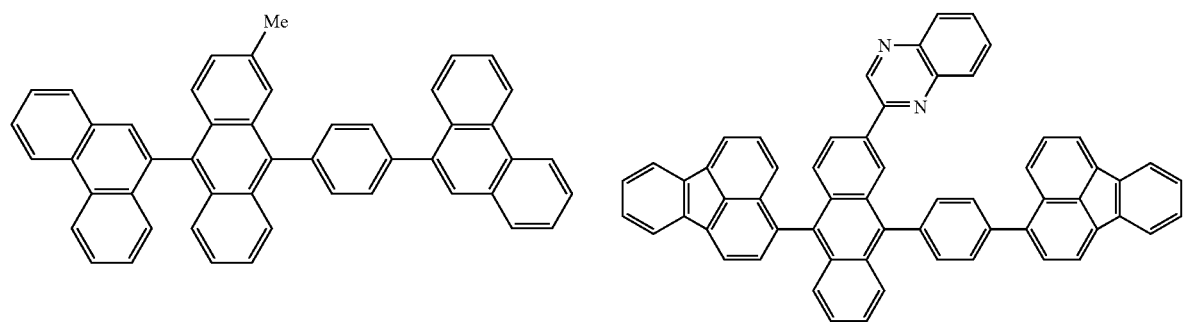
AN42
AN43
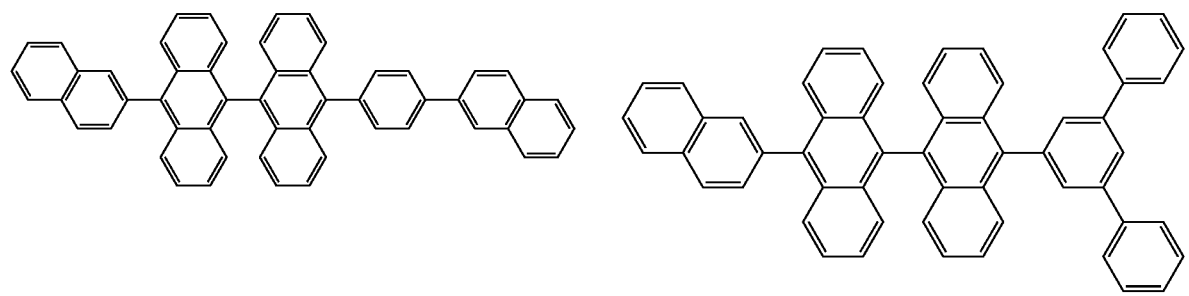
AN44
AN45
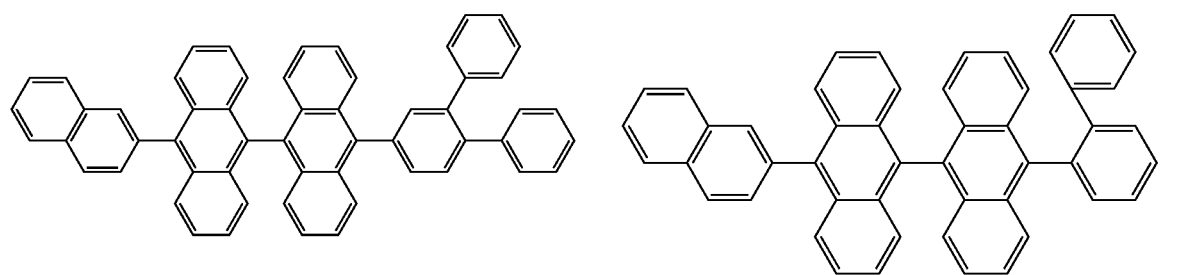
AN46

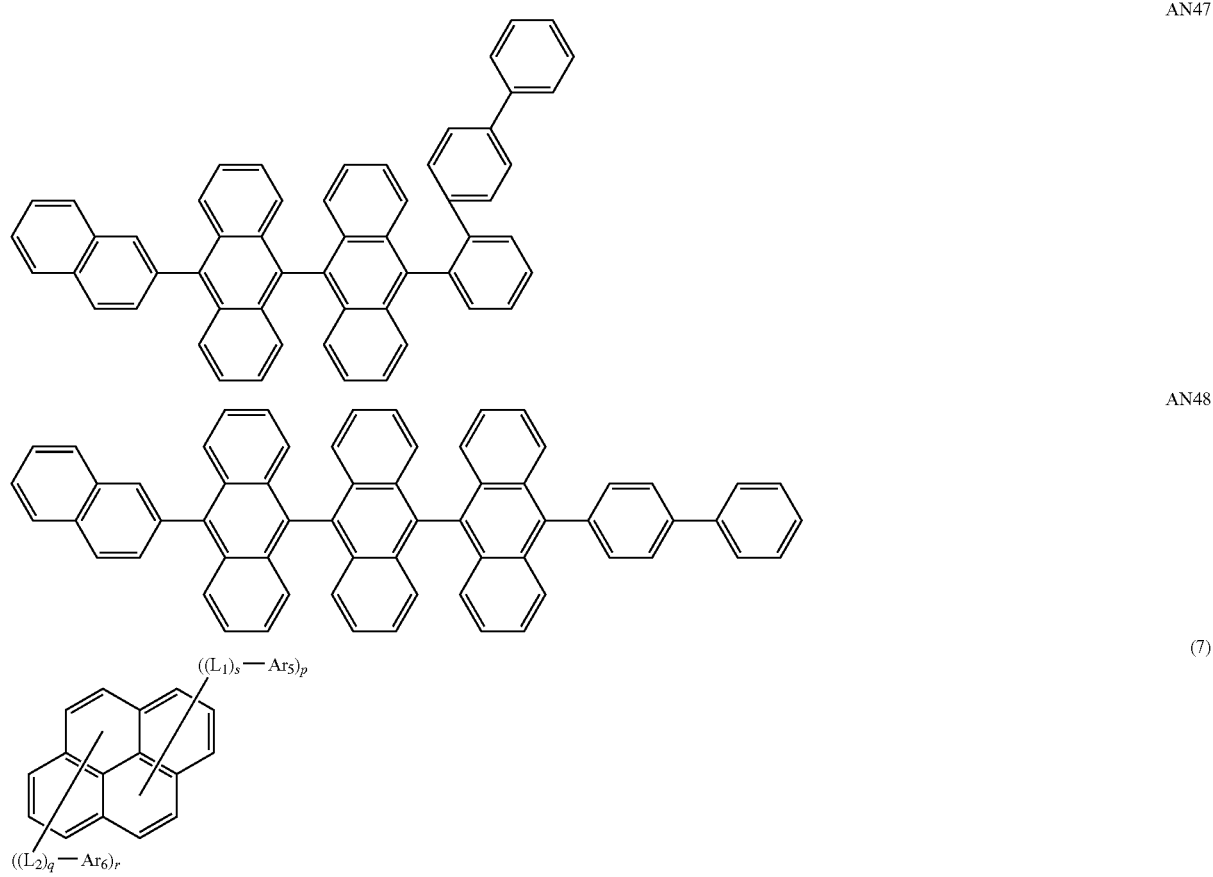

(7)

In the general formula (7), $Ar_5$ and $Ar_6$ each represents a substituted or unsubstituted aryl group having 6 to 50 nuclear carbon atoms; $L_1$ and $L_2$ each represents a substituted or unsubstituted phenylene group, a substituted or unsubstituted naphthalenylene group, a substituted or unsubstituted fluorenylene group or a substituted or unsubstituted dibenzosilolylene group; s represents an integer of 0 to 2, p represents an integer of 1 to 4, q represents an integer of 0 to 2 and r represents an integer of 0 to 4; and, $L_1$ or $Ar_5$ bonds to any one of 1 to 5 position of pyrene, also $L_2$ or $Ar_6$ bonds to any one of 6 to 10 position thereof.

However, when p+r is an even number, $Ar_5$, $Ar_6$, $L_1$ and $L_2$ satisfy a following requirement (1) or a requirement (2):

(1) $Ar_5 \neq Ar_6$ and/or $L \neq L'$ (wherein ≠ means that each group has a different structure)

(2) When $Ar_5 = Ar_6$ and $L_1 = L_2$ (2-1) s≠q and/or p≠r, or (2-2) when s=q and p=r, (2-2-1) both $L_1$ and $L_2$ or pyrene each bonds respectively to different positions of $Ar_5$ and $Ar_6$, or (2-2-2) both $L_1$ and $L_2$ or pyrene each bonds respectively to the same position of $Ar_5$ and $Ar_6$, excluding a case where a pyrene derivative having both $L_1$ and $L_2$ or both $Ar_5$ and $Ar_6$ bond to 1 and 6 positions thereof, or 2 and 7 positions thereof.

Specific examples and substituents of the $Ar_5$, $Ar_6$, $L_1$ and $L_2$ are the same as those explained about the foregoing general formulae (1) to (4).

Specific examples of the pyrene derivative represented by the general formula (7) will be shown below, though not particularly limited thereto.

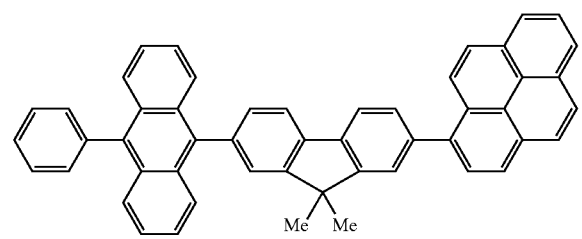

P1

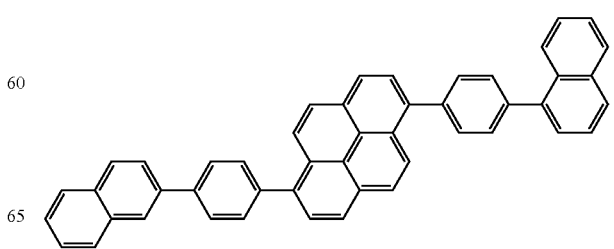

P2

-continued
P3
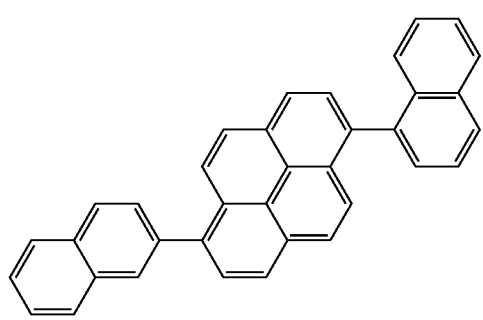
P4
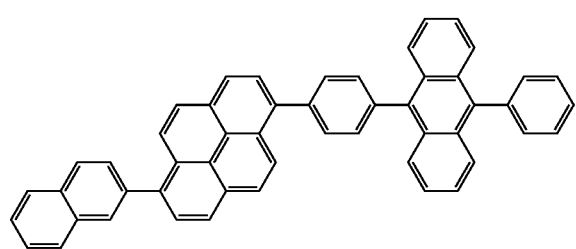
P5
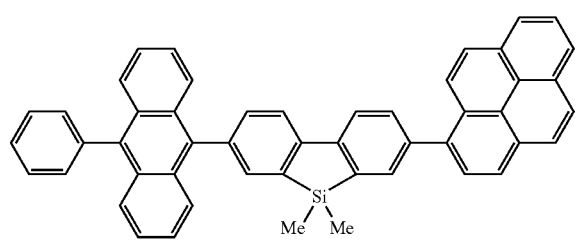
P6
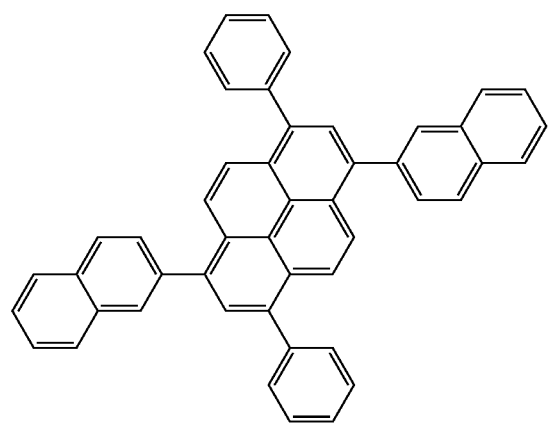
-continued
P7
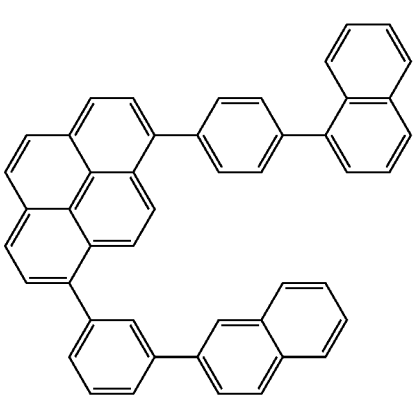
P8
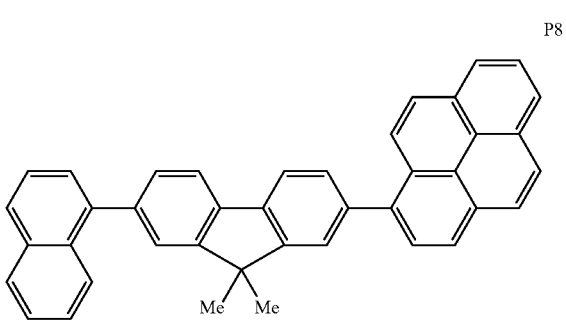
P9
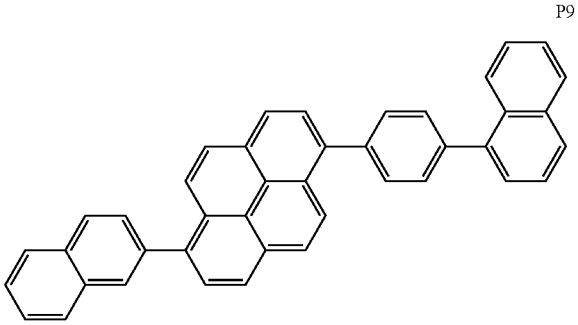
P10
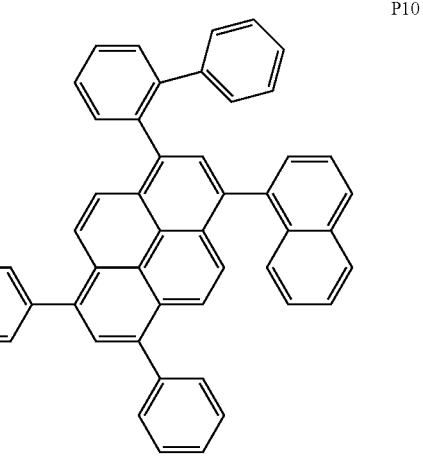

-continued
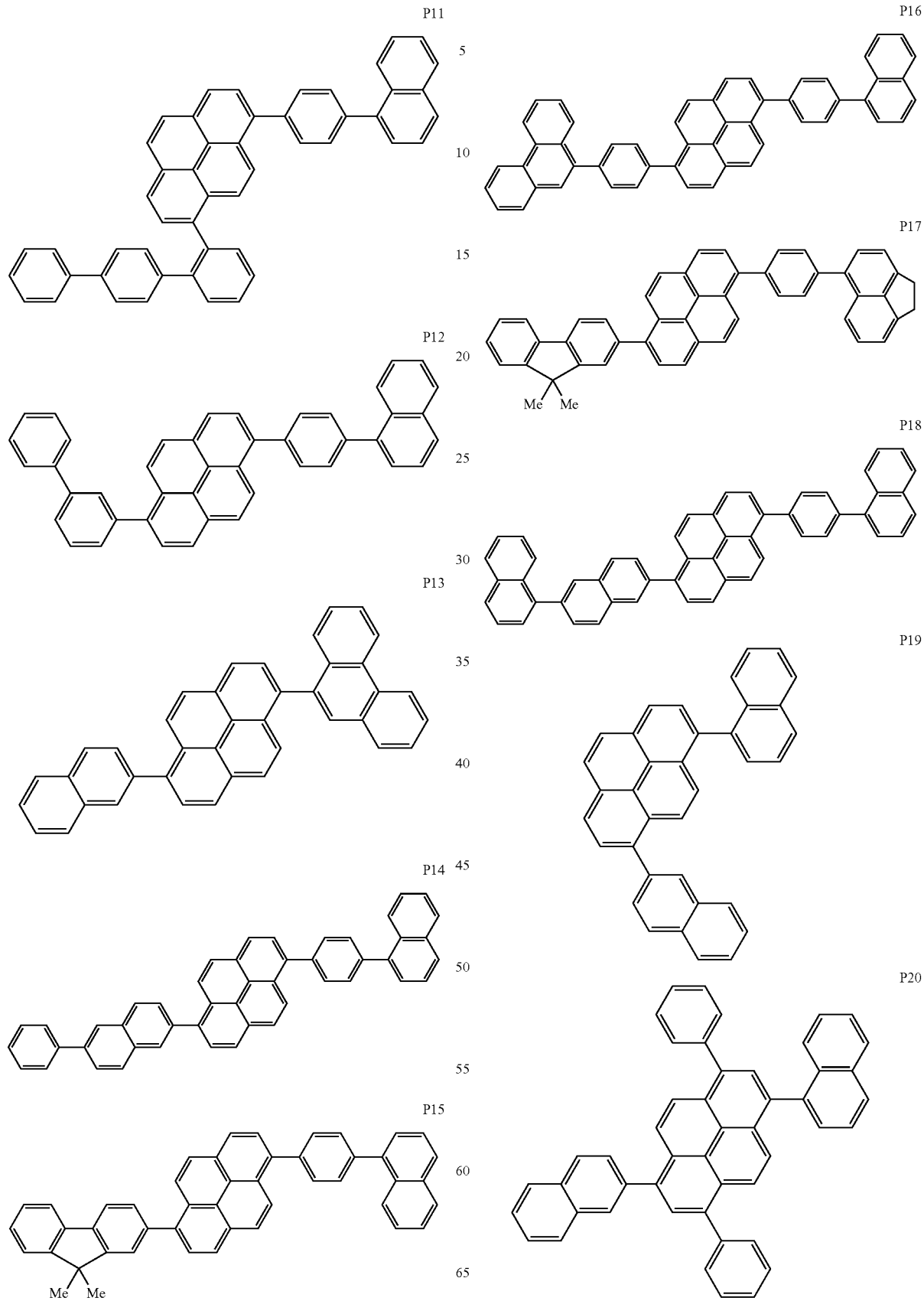

-continued

P21

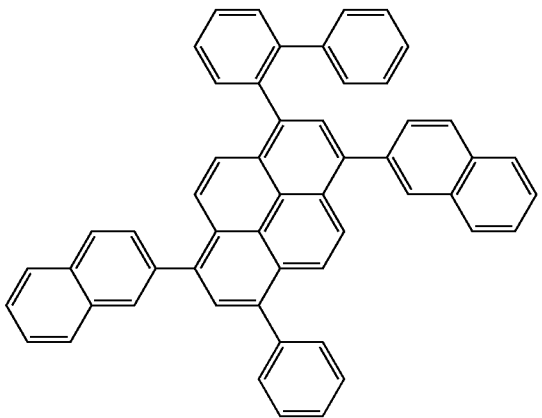

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The light emitting layer may also optionally contain, in addition to the aromatic amine derivatives of the present invention, conventionally known materials such as light emitting materials, doping materials, hole injecting materials and electron injecting materials according to requirements. The organic EL device having such a multilayer structure can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance of light emission and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may include a hole injecting layer into which holes are injected from the electrode, and a hole transporting layer for accepting the holes from the hole injecting layer and transporting the holes to the light emitting layer. Also, the multi-layer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the host material or the doping material besides the foregoing general formulae (5) to (7) employable for the light emitting layer together with the aromatic amine derivative of the present invention include condensed mass aromatic compound such as naphthalene, phenanthrene, rubrene, anthracene, tetracene, pyrene, perylene, chrysene, decacyclene, coronene, tetraphenylcyclopentadiene, pentaphenyl cyclopentadiene, fluorene, spiro fluorene, 9,10-diphenylanthracene, 9,10-bis(phenyl-ethynyl)anthracene, 1,4-bis(9'-ethynyl anthracenyl)benzene and those derivatives; organometallic complex such as tris(8-quinolinolat) aluminium, bis-(2-methyl-8-quinolinolat)-4-(phenylphenolinat) aluminium, etc.; triarylamine derivative, styryl amine derivative, stilbene derivative, coumarin derivative, pyran derivative, oxazone derivative, benzothiazole derivative, benzoxazole derivative, benzimidazole derivative, pyrazine derivative, cinnamate ester derivative, diketo pyrrolopyrrole derivative, acridone derivative, quinacridon derivative, etc.; though not particularly limited thereto.

The hole injecting material is preferably made of compounds which have a good hole transporting ability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenyl amine, styryl amine-type triphenyl amine, diamine-type triphenyl amine and derivatives thereof, as well as polyvinyl carbazoles, polysilanes, and high molecular materials such as conductive polymers, though not particularly limited thereto.

Of those hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, CLAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, such as the above hole transporting layer or hole injecting layer.

The electron injecting material is preferably made of compounds which have a good electron transporting ability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyrane dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhanced sensitization thereof.

In the organic EL device of the present invention, among these electron injecting materials, more effective electron injecting materials are metal complex compounds and nitrogen-containing five-member ring derivatives.

Specific examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, and bis(2-methyl-8-quinolinato) (2-naphtholato) gallium, though not particularly limited thereto. The nitrogen-containing five member ring derivatives are preferably derivatives of oxazole, thiazole, oxadiazole, thiadiazole or triazole.

Specific examples of the nitrogen-containing five member ring derivatives include 2,5-bis(1-phenyl)-1,3,4-oxazole, dimethyl POPOP, 2,5-bis(1-phenyl)-1,3,4-thiazole, 2,5-bis (1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the aromatic amine derivatives represented by the general formulae (1) to (4), at least one material selected from the group consisting of light emitting materials, doping materials, hole injecting materials and electron injecting materials. The organic EL device of the present invention may be further provided on a surface thereof with a protective layer, or the whole part thereof may be protected with silicone oil, resins, etc., in order to enhance a stability thereof against temperature, humidity, atmosphere, etc.

The anode of the organic EL device according to the present invention may be suitably made of a electroconductive material having a work function more than 4 eV. Examples of the electroconductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic conductive resins such as polythiophene and polypyrrole. The cathode of the organic EL device according to the present invention may be suitably made of a electroconductive material having a work function of 4 eV or smaller. Examples of the electroconductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above electroconductive material by vapor deposition method, sputtering method, etc., so as to ensure a desirable transparency thereof. The electrode disposed on a light emitting surface of the device preferably has a light transmittance of 10% or more. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluororethylene-hexafluoropropylene copolymer, polychlorotrifluoroethylene, polyvinylidene fluoride, polyesters, polycarbonates, polyurethanes, polyimides, and polyether imides.

The respective layers of the organic EL device of the present invention may be formed by either a dry film-forming process such as vacuum deposition, sputtering, plasma and ion-plating, or a wet film-forming process such as spin-coating, dipping and flow-coating. The thickness of the respective layers is not particularly limited, but should be adjusted to an appropriate range. When the thickness is too large, a great electric voltage must be applied to the device in order to achieve a predetermined light output, resulting in a poor efficiency of light emission. On the other hand, when the thickness is too thin, pinholes tend to be formed in the layers, thereby failing to obtain a sufficient luminance of light emission even upon applying an electric field thereto. The suitable thickness of the respective layers is usually in the range of from 5 nm to 10 µm and preferably from 10 nm to 0.2 µm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and conductive resins such as polythiophene and polypyrrole. Examples of the additives include antioxidants, ultraviolet absorbers and plasticizers.

The organic EL device of the present invention is suitably applied to, for example, surface light-emitting members such as a wall-type TV flat panel displays, light sources for copiers, printers, back light for liquid crystal displays and, measuring equipments, display panels, marker light, etc. Further, the material of the present invention can be used not only for organic EL devices but also in other applications such as electrophotographic members, photoelectric converters, solar cells, image sensors, etc.

EXAMPLES

The present invention will be described in more detail by reference to the following examples.

Synthesis Example 1

Synthesis of Compound (5)

Under an atmospheric argon gas flow, 4,8-dimethyl-6,12-dibromochrysene in an amount of 3.1 g (10 mmol), 2-dinaphthylamine in an amount of 6.7 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.2 g of pale yellow powders were obtained. The pale yellow powders were identified as Compound (5) from the result of NMR spectrum (FIG. 1) and in accordance with Field Desorption Mass Spectrum (FD-MS) measurement (yield: 90%). The NMR spectrum was obtained by means of DRX-500 (Trade name; produced by Brucker Optics Inc.).

Synthesis Example 2

Synthesis of Compound (9)

Figure 2:
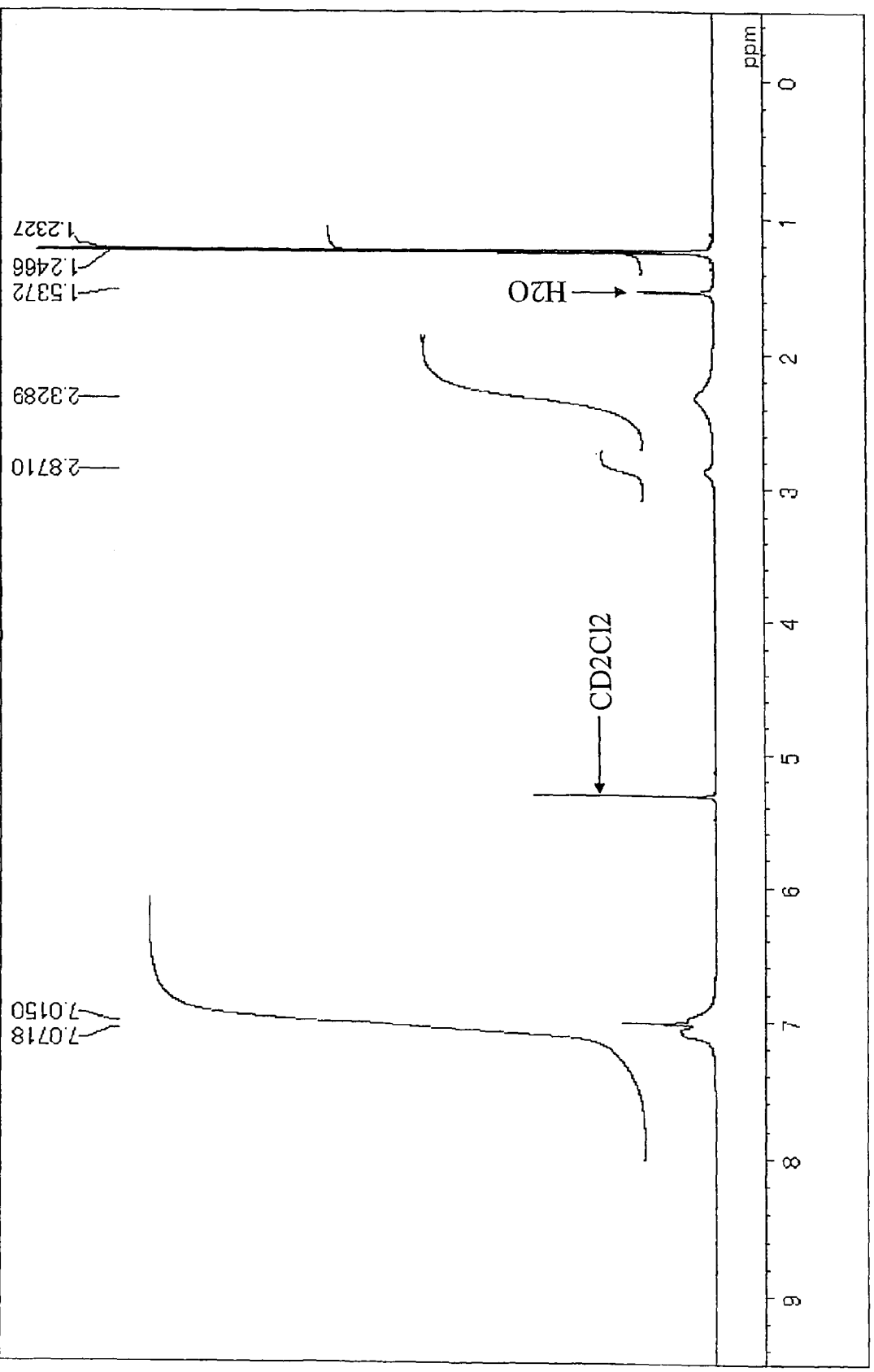
FIG. 2 is a chart showing a NMR spectrum about Compound (9) as the aromatic amine derivative of the present invention.

Under an atmospheric argon gas flow, 2-isopropyl-6,12-dibromochrysene in an amount of 4.2 g (10 mmol), 4-isopropylphenyl-p-tolyl amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 5.6 g of pale yellow powders were obtained. The pale yellow powders were identified as Compound (9) from the result of NMR spectrum (FIG. 2) and in accordance with FD-MS measurement (yield: 94%). The NMR spectrum was obtained by means of DRX-500 (Trade name; produced by Brucker Optics Inc.).

Synthesis Example 3

Synthesis of Compound (21)

Figure 3:
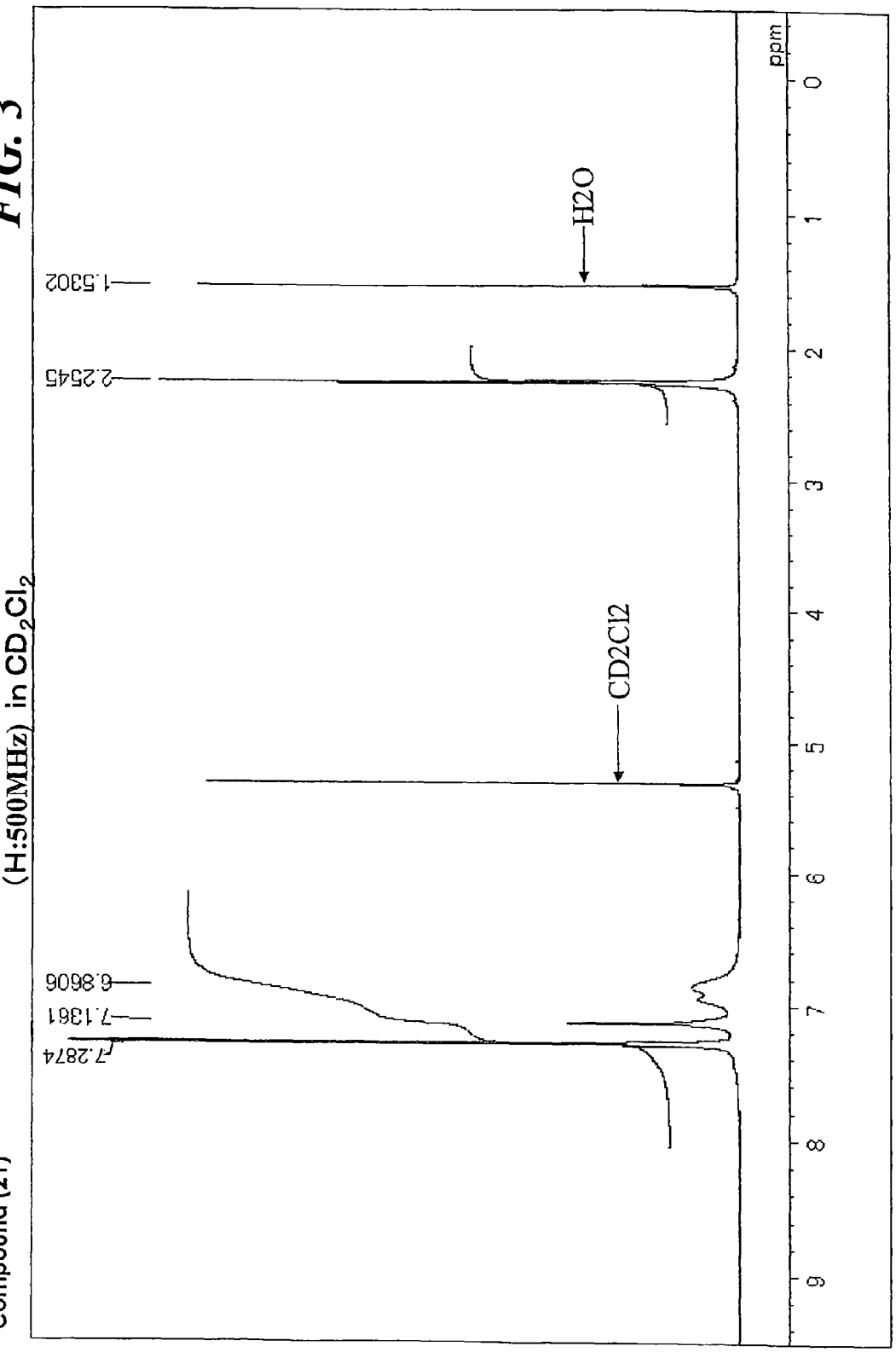
FIG. 3 is a chart showing a NMR spectrum about Compound (21) as the aromatic amine derivative of the present invention.

Under an atmospheric argon gas flow, 4,8-diphenyl-2,6-dibromonaphthalene in an amount of 4.3 g (10 mmol), m,m-ditolylamine in an amount of 4.9 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 5.6 g of pale yellow powders were obtained. The pale yellow powders were identified as Compound (21) from the result of NMR spectrum (FIG. 3) and in accordance with FD-MS measurement (yield: 75%). The NMR spectrum was obtained by means of DRX-500 (Trade name; produced by Brucker Optics Inc.).

Synthesis Example 4

Synthesis of Compound (22)

Figure 4:
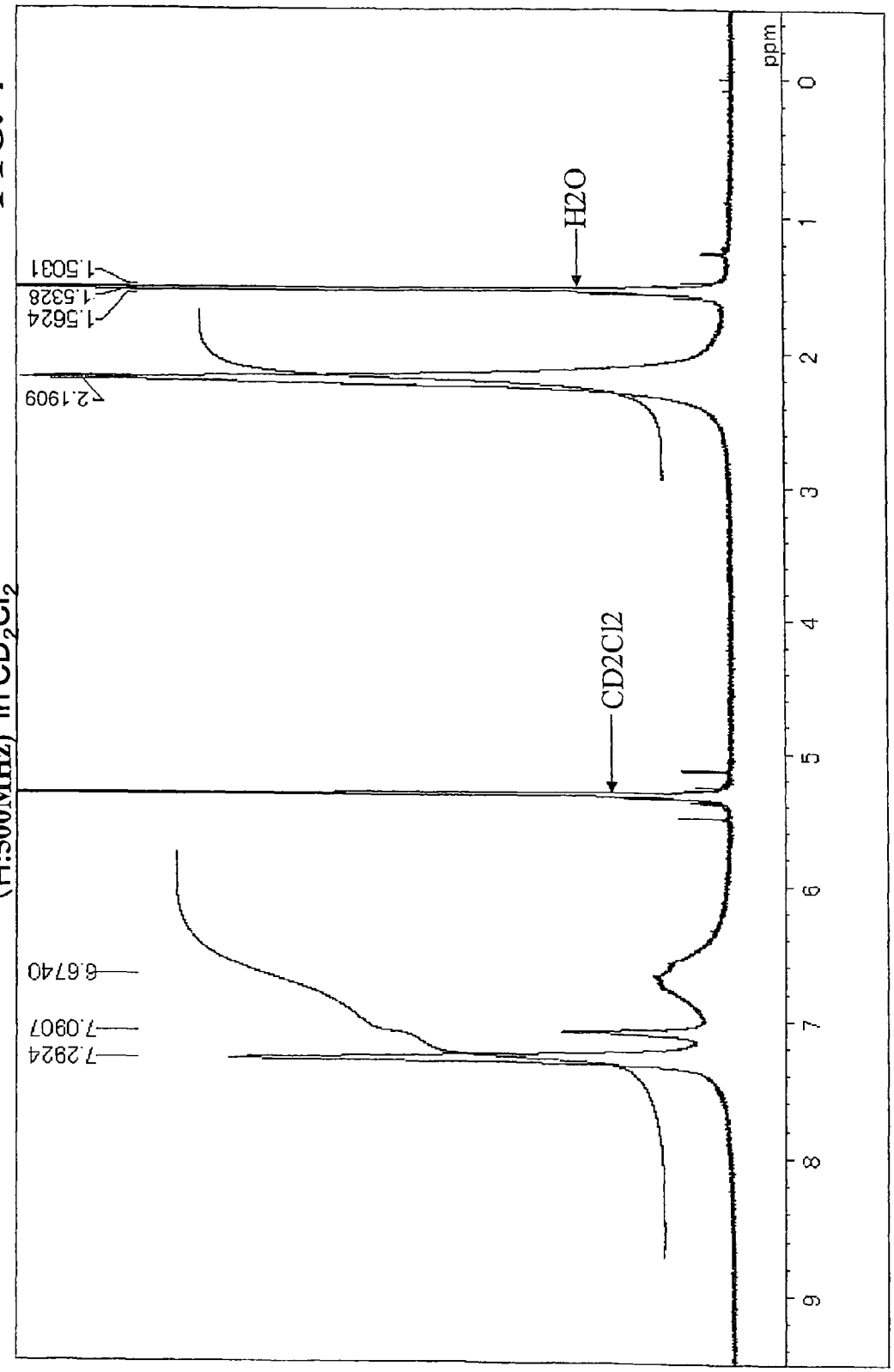
FIG. 4 is a chart showing a NMR spectrum about Compound (22) as the aromatic amine derivative of the present invention.

Under an atmospheric argon gas flow, 4,8-diphenyl-2,6-dibromonaphthalene in an amount of 4.3 g (10 mmol), bis(3,5-dimethylphenyl)amine in an amount of 5.6 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 5.6 g of pale yellow powders were obtained. The pale yellow powders were identified as Compound (22) from the result of NMR spectrum (FIG. 4) and in accordance with FD-MS measurement (yield: 94%). The NMR spectrum was obtained by means of DRX-500 (Trade name; produced by Brucker Optics Inc.).

Synthesis Example 5

Synthesis of Compound (26)

Figure 5:
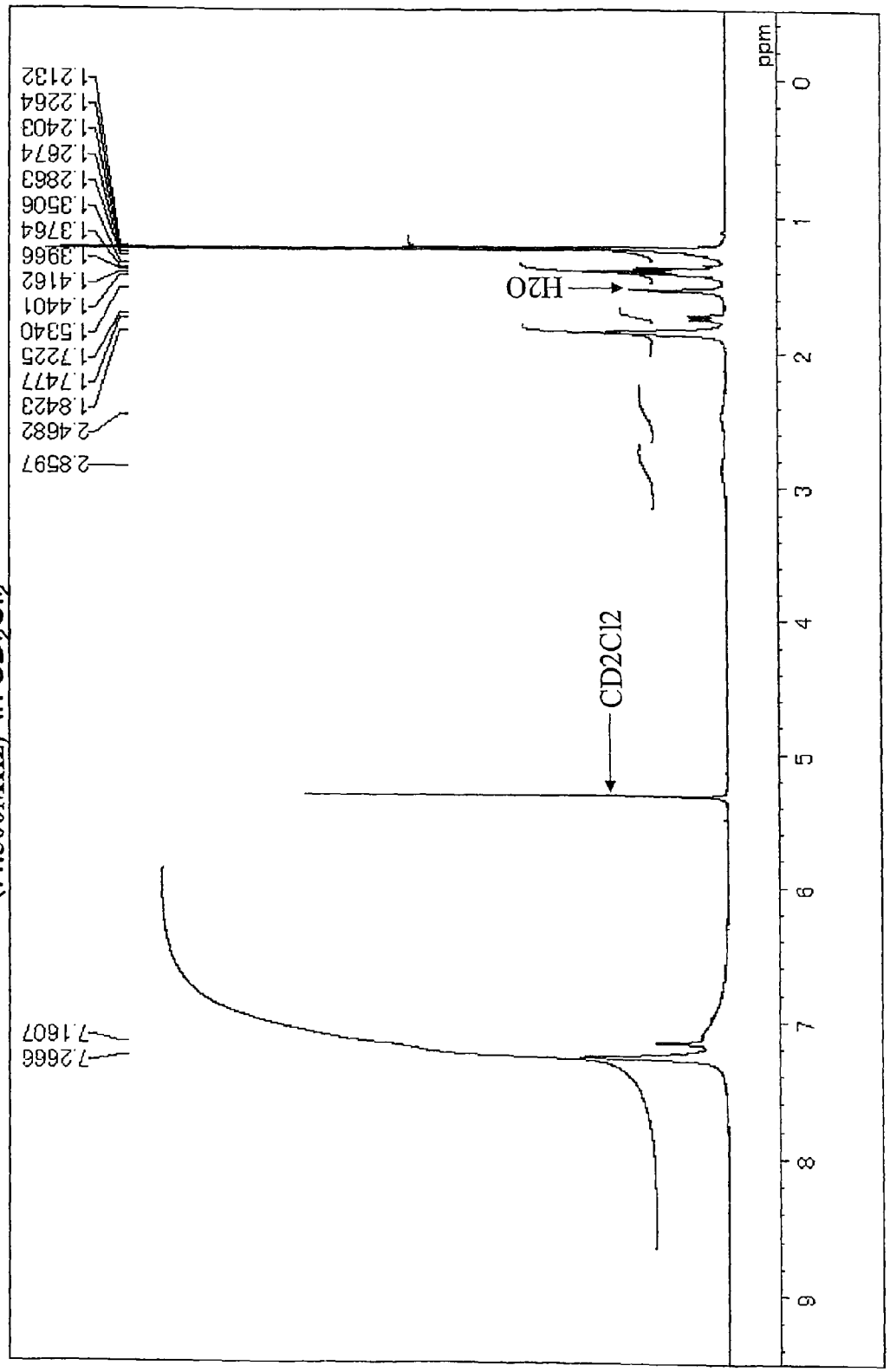
FIG. 5 is a chart showing a NMR spectrum about Compound (26) as the aromatic amine derivative of the present invention.

Under an atmospheric argon gas flow, 4,8-diphenyl-2,6-dibromonaphthalene in an amount of 4.3 g (10 mmol), 4-isopropyl-4'-cyclohexyl diphenylamine in an amount of 7.5 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 8.2 g of pale yellow powders were obtained. The pale yellow powders were identified as Compound (26) from the result of NMR spectrum (FIG. 5) and in accordance with FD-MS measurement (yield: 95%). The NMR spectrum was obtained by means of DRX-500 (Trade name; produced by Brucker Optics Inc.).

Example 1

Fabrication of Organic EL Device

A 120 nm-thick transparent electrode made of indium oxide was formed on a glass substrate having a size of 25 mm×75 mm×1.1 mm. The glass substrate with the transparent electrode was cleaned by irradiation of Ultra Violet ray and ozone. The thus cleaned glass substrate with the transparent electrode was mounted to a vacuum vapor deposition apparatus.

First, N',N"-bis[4-(diphenylamino)phenyl]-N',N"-diphenylbiphenyl-4,4'-diamine was vapor-deposited to form a hole injecting layer having a thickness of 60 nm, and then N,N,N',N'-tetrakis(4-biphenyl)-4,4'-bendizine was vapor-deposited on the hole injecting layer to form a hole transporting layer having a thickness of 20 nm. Then, 10,10'-bis[1,1',4',1"]terphenyl-2-yl-9,9'-bianthracenyl and the above Compound (9) were simultaneously vapor-deposited at a weight ratio of 40:2 on the hole transporting layer to form a light emitting layer having a thickness of 40 nm.

Next, tris(8-hydroxyquinolinato)aluminum was vapor-deposited on the light emitting layer to form an electron injecting layer having a thickness of 20 nm. Then, lithium fluoride was vapor-deposited to form a layer having a thickness of 1 nm, and further aluminum was vapor-deposited thereon to form an aluminum layer having a thickness of 150 nm. The aluminum/lithium fluoride layer functioned as a cathode. Thus, an organic EL device was fabricated.

As a result of subjecting the thus obtained organic EL device to a test by feeding electric current, it was confirmed that a blue light with a luminance of 300 cd/m$^2$ (peak wavelength of light emission: 455 nm; CIEx=0.154, CIEy=0.157) and current efficiency of 3 cd/A was emitted at a voltage of 7.0 V and a current density of 10 mA/cm$^2$. Further, as a result of subjecting the device to a continuous test by feeding DC electric current starting at an initial luminance of 1,000 cd/m$^2$, it was confirmed that the half lifetime thereof was 1,500 hours.

Example 2

Fabrication of Organic EL Device

An organic EL device was fabricated in accordance with the same procedures as those conducted in Example 1 except that Compound (5) was replaced with Compound (22).

As a result of subjecting the thus obtained organic EL device to a test by feeding electric current, it was confirmed that a blue light with a luminance of 700 cd/m$^2$ (peak wavelength of light emission: 480 nm; CIEx=0.173, CIEy=0.305) and current efficiency of 7 cd/A was emitted at a voltage of 7.5 V and a current density of 10 mA/cm$^2$. Further, as a result of subjecting the device to a continuous test by feeding DC electric current starting at an initial luminance of 2,000 cd/m$^2$, it was confirmed that the half lifetime thereof was 2,000 hours or longer.

Comparative Example 1

An organic EL device was fabricated in accordance with the same procedures as those conducted in Example 1 except that Compound (5) was replaced with 2,6-bis(2-naphthylamino)naphthalene.

As a result of subjecting the thus obtained organic EL device to a test by feeding electric current, it was confirmed that a blue light with a luminance of 150 cd/m$^2$ (peak wavelength of light emission: 453 nm; CIEx=0.154, CIEy=0.150) and current efficiency of 1.5 cd/A was emitted at a voltage of 7.5 V and a current density of 10 mA/cm$^2$. Further, as a result of subjecting the device to a continuous test by feeding DC electric current starting at an initial luminance of 2,000 cd/m$^2$, it was confirmed that the half lifetime thereof was as short as 500 hours.

From the above-mentioned result, it is apparent that when a compound without any substituent to diaminonaphthalene skeleton was employed as a material of an organic EL device, a wavelength of the color of light emission lengthens, current efficiency, luminance and lifetime are inferior because of an association between compounds each other.

Example 3

Fabrication of Organic EL Device

An organic EL device was fabricated in accordance with the same procedures as those conducted in Example 1 except that the Compound (I) was replaced with N,N,N',N'-tetrakis(4-biphenyl)-4,4'-benzidine as the hole transporting material.

As a result of subjecting the thus obtained organic EL device to a test by feeding electric current, it was confirmed that a blue light with a luminance of 290 cd/m$^2$ (peak wavelength of light emission: 455 nm; CIEx=0.154, CIEy=0.152) and current efficiency of 7 cd/A was emitted at a voltage of 7.0 V and a current density of 10 mA/cm$^2$. Further, as a result of subjecting the device to a continuous test by feeding DC electric current starting at an initial luminance of 1,000 cd/m$^2$, it was confirmed that the half lifetime thereof was 1,400 hours or longer.

INDUSTRIAL APPLICABILITY

The organic EL device using the aromatic amine derivative represented by any one of the general formulae (1) to (4) according to the present invention exhibits excellent luminance and enhanced efficiency of light emission and further, the device is free from deterioration in properties even after being used for a long period of time and, therefore, has a prolonged lifetime. Therefore, they are highly applicable as the organic EL devices having practical performance.

What is claimed is:

1. An aromatic amine derivative represented by the following formula (3):

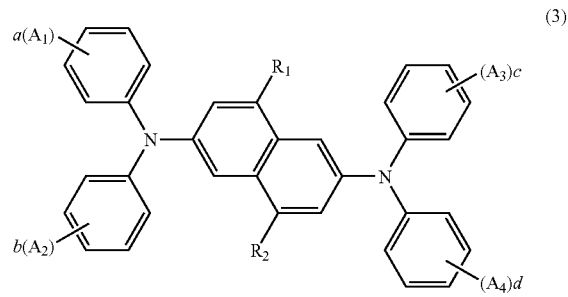

wherein R$_1$ and R$_2$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom;

$A_1$ to $A_4$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group or a halogen atom;

a, b, c and d each independently represents an integer of 0 to 5, when a, b, c and d each are 2 or greater, $A_1$ to $A_4$ may be the same with or different from each other, and may bond each other to form a saturated or unsaturated ring; and further an $A_1$ and an $A_2$, and an $A_3$ and an $A_4$ may bond each other to form a saturated or unsaturated ring;

wherein both of $R_1$ and $R_2$ cannot be hydrogen atoms at the same time and wherein at least one of a, b, c and d is an integer of 2 or greater.

2. The aromatic amine derivative according to claim 1, wherein at least one of $A_1$ to $A_4$ represents a substituted or unsubstituted silyl group.

3. The aromatic amine derivative according to claim 1, which is a doping material for an organic electroluminescence device.

4. An organic electroluminescence device which comprises at least one organic thin film layer comprising a light emitting layer sandwiched between a pair of electrodes consisting of an anode and a cathode, wherein at least one of the at least one organic thin film layer comprises at least one aromatic amine derivative according to claim 1.

5. The organic electroluminescence device according to claim 4, which comprises said at least one aromatic amine derivative between said anode and said light emitting layer.

6. The organic electroluminescence device according to claim 4, wherein said light emitting layer comprises said at least one aromatic amine derivative in an amount of 0.1 to 20% by weight.

7. The organic electroluminescence device according to claim 4, which emits bluish light.

8. An aromatic amine derivative represented by the following formula (4):

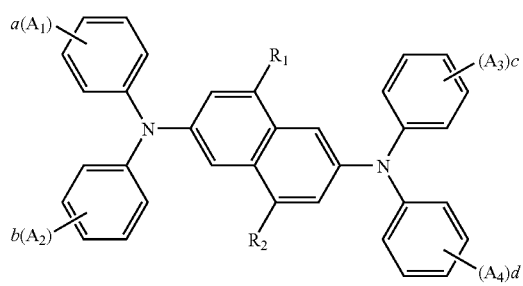

wherein $R_1$ and $R_2$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom;

$A_1$ to $A_4$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group or a halogen atom;

a, b, c and d each independently represents an integer of 0 to 5, when a, b, c and d each are 2 or greater, $A_1$ to $A_4$ may be the same with or different from each other, and may bond each other to form a saturated or unsaturated ring; and further, an $A_1$ and an $A_2$, and an $A_3$ and an $A_4$ may bond each other to form a saturated or unsaturated ring;

wherein at least one of $R_1$ and $R_2$ is a substituted or unsubstituted secondary or tertiary alkyl group having 3 to 10 carbon atoms, wherein all of $A_1$ to $A_4$ cannot be hydrogen atoms at the same time, and wherein at least one of $A_1$ to $A_4$ represents a substituted or unsubstituted silyl group.

9. The aromatic amine derivative according to claim 8, which is a doping material for an organic electroluminescence device.

10. An organic electroluminescence device which comprises at least one organic thin film layer comprising a light emitting layer sandwiched between a pair of electrodes consisting of an anode and a cathode, wherein at least one of the at least one organic thin film layer comprises at least one aromatic amine derivative according to claim 8.

11. The organic electroluminescence device according to claim 10, which comprises said at least one aromatic amine derivative between said anode and said light emitting layer.

12. The organic electroluminescence device according to claim 10, wherein said light emitting layer comprises said at least one aromatic amine derivative in an amount of 0.1 to 20% by weight.

13. The organic electroluminescence device according to claim 10, which emits bluish light.

* * * * *